(12) United States Patent
Nitta et al.

(10) Patent No.: US 10,338,175 B2
(45) Date of Patent: Jul. 2, 2019

(54) MAGNETIC RESONANCE IMAGING APPARATUS AND MEDICAL IMAGE PROCESSING METHOD

(71) Applicant: TOSHIBA MEDICAL SYSTEMS CORPORATION, Otawara-Shi (JP)

(72) Inventors: Shuhei Nitta, Ota (JP); Tomoyuki Takeguchi, Kawasaki (JP); Yurika Ogawa, Yokohama (JP); Kensuke Shinoda, Otawara (JP); Takuya Fujimaki, Otawara (JP); Syuhei Takemoto, Otawara (JP); Shigehide Kuhara, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 672 days.

(21) Appl. No.: 14/947,500

(22) Filed: Nov. 20, 2015

(65) Prior Publication Data
US 2016/0146914 A1 May 26, 2016

(30) Foreign Application Priority Data
Nov. 20, 2014 (JP) .................. 2014-236035

(51) Int. Cl.
  *G01R 33/483* (2006.01)
  *A61B 8/00* (2006.01)
  *G01R 33/54* (2006.01)

(52) U.S. Cl.
  CPC .......... *G01R 33/4835* (2013.01); *A61B 8/463* (2013.01); *G01R 33/546* (2013.01)

(58) Field of Classification Search
  CPC .. G06T 2219/028; G16H 40/63; G16H 30/20; G16H 30/40; G01R 33/546;
  (Continued)

(56) References Cited

U.S. PATENT DOCUMENTS 6,381,296 B1 4/2002 Nishiura
7,280,862 B2 10/2007 Gupta et al.
(Continued)

FOREIGN PATENT DOCUMENTS

JP 2002-140689 A 5/2002
JP 2006-55641 A 3/2006
(Continued)

OTHER PUBLICATIONS

"CMR Image Acquisition Protocols" Society for Cardiovascular Magnetic Resonance (SCMR), Version 1.0, Mar. 2007, 31 Pages (with English language translation).
(Continued)

*Primary Examiner* — Son T Le
*Assistant Examiner* — Dustin R Dickinson
(74) *Attorney, Agent, or Firm* — Oblon, McClelland, Maier & Neustadt, L.L.P.

(57) ABSTRACT

A magnetic resonance imaging apparatus according to an embodiment includes processing circuitry. The processing circuitry generates a plurality of cross-sectional images for setting a sectional position to be collected in main imaging based on a characteristic portion of a target detected in three-dimensional data. The processing circuitry lists the cross-sectional images on a display and superimposes a mark corresponding to the characteristic portion on at least one of the cross-sectional images. The processing circuitry receives a setting operation to determine the sectional position. The processing circuitry causes, when the mark is selected in the setting operation, a cross-sectional image to be emphasized a sectional position of which is defined using the characteristic portion corresponding to the mark among the listed cross-sectional images. The processing circuitry performs main imaging based on the sectional position after the setting operation.

10 Claims, 17 Drawing Sheets

(58) Field of Classification Search
CPC .............. G01R 33/5608; G01R 33/283; G01R 33/4835; A61B 6/463; A61B 5/055
See application file for complete search history.

(56) References Cited

U.S. PATENT DOCUMENTS

| | | | |
|---|---|---|---|
| 7,408,528 | B2 | 8/2008 | Gunji |
| 8,928,318 | B2 | 1/2015 | Nitta et al. |
| 9,098,927 | B2 | 8/2015 | Nitta et al. |
| 2005/0015359 | A1* | 1/2005 | Kidalka ............ G06F 17/30067 |
| 2005/0089138 | A1* | 4/2005 | Toth ........................ A61B 6/032 378/20 |
| 2013/0129168 | A1* | 5/2013 | Ross ..................... G06T 7/0012 382/128 |
| 2014/0176561 | A1 | 6/2014 | Nakamura |
| 2015/0150454 | A1 | 6/2015 | Nitta et al. |

FOREIGN PATENT DOCUMENTS

| | | |
|---|---|---|
| JP | 1018303 B2 | 9/2007 |
| JP | 4460973 B2 | 5/2010 |
| JP | 2012-110689 A | 6/2012 |
| JP | 5323191 82 | 10/2013 |
| JP | 5325951 B2 | 10/2013 |
| JP | 2014-121596 A | 7/2014 |
| JP | 5587614 B2 | 9/2014 |

OTHER PUBLICATIONS

Christopher M. Kramer, et al., "Standardized cardiovascular magnetic resonance imaging (CMR) protocols, society for cardiovascular magnetic resonance: board of trustees task force on standardized protocols" Journal of Cardiovascular Magnetic Resonance, vol. 10:35, 2008, 10 Pages.

"Mitral Valve Study: Step by Step Mitral Valve Flow" Society for Cardiovascular Magnetic Resonance (SCMR), http://scmr.org/assets/files/technologists/mitral_valve.pdf, Dec. 10, 2005, 3 Pages.

"Aortic Valve Study: Step by Step AO Function and Flow" Society for Cardiovascular Magnetic Resonance (SCMR), http://scmr org/assets/files/technologists/aoflow pdf, Mar. 2, 2005. 6 Pages.

"Cardiac MRI: Planning the basic cardiac views" Society for Cardiovascular Magnetic Resonance (SCMR), http://scmr.org/assets/files/members/documents/Cardiac_views.pdf, 2001, 2 Pages.

Japanese Office Action dated Sep. 11, 2018 in Patent Application No. 2014-236035.

\* cited by examiner

FIG.7

| ID | DEFINITION PARAMETER |
|---|---|
| L4CH | MITRAL VALVE, TRICUSPID VALVE, LEFT VENTRICULAR APEX OF HEART |
| ⋮ | ⋮ |

23a

MAGNETIC RESONANCE IMAGING APPARATUS AND MEDICAL IMAGE PROCESSING METHOD

CROSS-REFERENCE TO RELATED APPLICATION

This application is based upon and claims the benefit of priority from Japanese Patent Application No. 2014-236035, filed on Nov. 20, 2014; the entire contents of which are incorporated herein by reference.

FIELD

Embodiments described herein relate generally to a magnetic resonance imaging apparatus.

BACKGROUND

Magnetic resonance imaging (MRI) is an imaging method of magnetically exciting nuclear spin of a subject placed in a static magnetic field with radio frequency (RF) pulses at the Larmor frequency, and reconstructing an image from a nuclear magnetic resonance (NMR) signal generated according to the excitation.

For example, a standardized protocol has been determined for a cardiac testing method with the MRI. In the standardized protocol, for example, determined is a procedure of collecting a multi-slice image (axial multi-slice) including a plurality of transverse sections after collecting a transverse cross-sectional image (axial), a sagittal cross-sectional image (sagittal), and a coronal cross-sectional image (coronal) that are called a scout image (scout) or a locator image (locator), and thereafter, collecting a reference cross-sectional image.

The reference cross-sectional image is a cross-sectional image based on anatomical features of the heart, and examples of the reference cross-sectional image include a left ventricular vertical long-axis image, a left ventricular horizontal long-axis image, a left/right ventricular short-axis image, a left/right ventricular 2-chamber long-axis image, a left/right ventricular 3-chamber long-axis image, a left/right ventricular 4-chamber long-axis image, a left/right ventricular outflow tract image, an aorta valve image, and a pulmonary valve image. A method of setting the reference cross-sectional image is determined for various targets such as a brain, a shoulder, and a knee.

BRIEF DESCRIPTION OF THE DRAWINGS

FIG. 7 is a diagram illustrating an example of a data structure of a sectional position definition information table according to the first embodiment;

DETAILED DESCRIPTION

A magnetic resonance imaging apparatus according to an embodiment includes processing circuitry. The processing circuitry generates a plurality of cross-sectional images for setting a sectional position to be collected in main imaging based on a characteristic portion of a target detected in three-dimensional data. The processing circuitry lists the cross-sectional images on a display and superimposes a mark corresponding to the characteristic portion on at least one of the cross-sectional images. The processing circuitry receives a setting operation to determine the sectional position. The processing circuitry causes, when the mark is selected in the setting operation, a cross-sectional image to be emphasized a sectional position of which is defined using the characteristic portion corresponding to the mark among the listed cross-sectional images. The processing circuitry performs main imaging based on the sectional position after the setting operation.

The following describes the magnetic resonance imaging apparatus (hereinafter, appropriately referred to as a "magnetic resonance imaging (MRI) apparatus") according to the embodiment with reference to the drawings. The embodi-

First Embodiment

Figure 1:
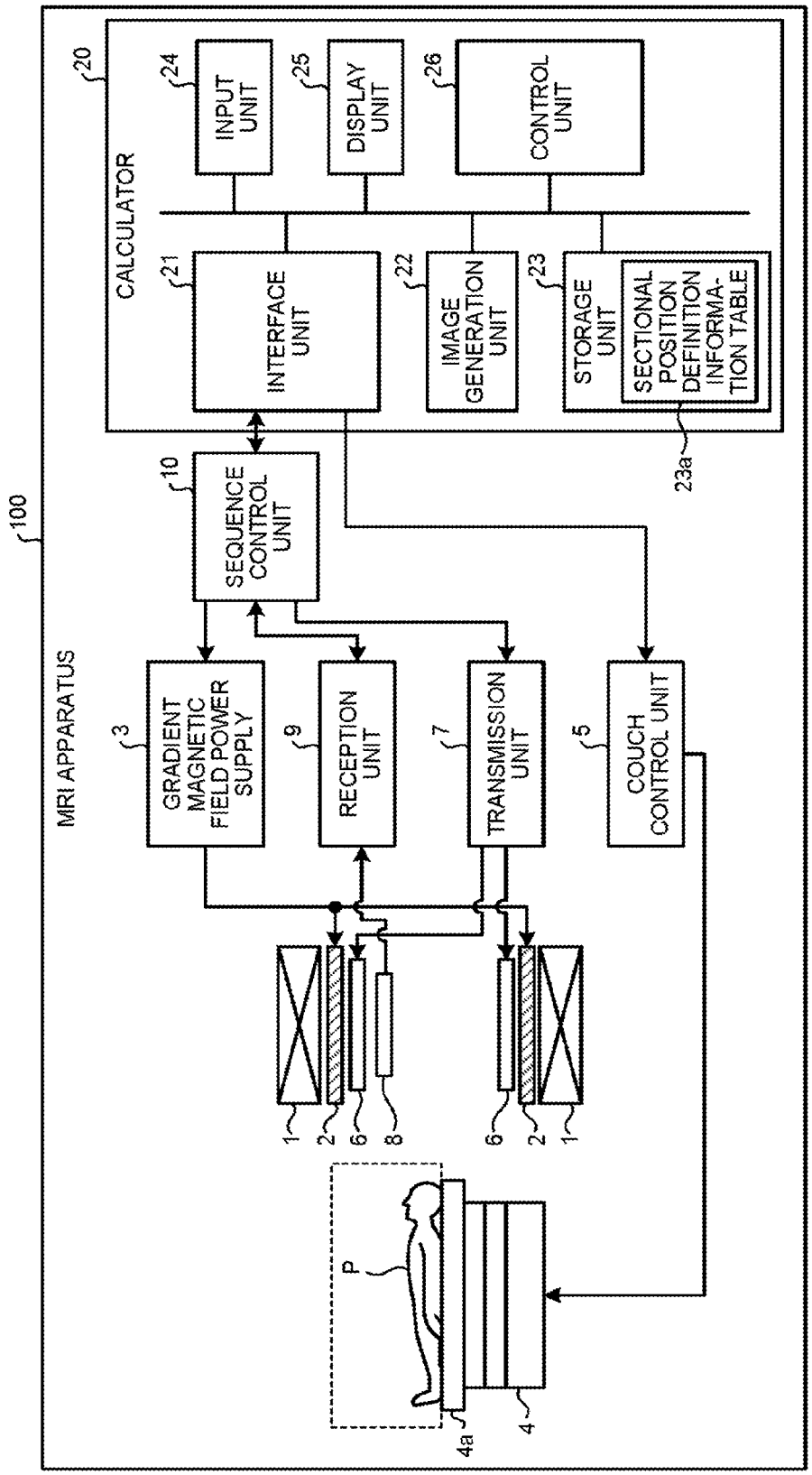
FIG. 1 is a functional block diagram illustrating an MRI apparatus according to a first embodiment.

FIG. 1 is a functional block diagram illustrating an MRI apparatus 100 according to a first embodiment. As illustrated in FIG. 1, the MRI apparatus 100 includes a static magnetic field magnet 1, a gradient coil 2, a gradient magnetic field power supply 3, a couch 4, a couch control unit 5, a transmission coil 6, a transmission unit 7, a reception coil 8, a reception unit 9, a sequence control unit 10, and a calculator 20. The MRI apparatus 100 does not include a subject P (for example, a human body) illustrated in a frame of a dotted line in FIG. 1. The MRI apparatus 100 illustrated in FIG. 1 is merely an example. For example, the sequence control unit 10 and components in the calculator 20 may be configured to be appropriately integrated or separated.

The static magnetic field magnet 1 is a magnet formed to have a hollow cylindrical shape (including a shape having an elliptic cross section that is orthogonal to an axis of a cylinder), and generates a static magnetic field in a space inside thereof. The static magnetic field magnet 1 is, for example, a permanent magnet. The static magnetic field magnet 1 may also be a superconducting magnet. When the static magnetic field magnet 1 is the superconducting magnet, the MRI apparatus 100 includes a static magnetic field power supply (not illustrated), and the static magnetic field power supply supplies electric current to the static magnetic field magnet 1. In this case, the static magnetic field magnet 1 receives the electric current supplied from the static magnetic field power supply to be excited. The static magnetic field power supply may be provided separately from the MRI apparatus 100.

The gradient coil 2 is a coil formed to have a hollow cylindrical shape (including a shape having an elliptic cross section that is orthogonal to an axis of a cylinder), and is arranged inside the static magnetic field magnet 1. The gradient coil 2 is formed by combining three coils corresponding to axes of X, Y, and Z orthogonal to each other. The three coils individually receive the electric current supplied from the gradient magnetic field power supply 3 and generate a gradient magnetic field in which magnetic field intensity varies along each of the axes of X, Y, and Z. Examples of gradient magnetic fields along the axes of X, Y, and Z generated by the gradient coil 2 include a gradient magnetic field Gs for slicing, a gradient magnetic field Ge for phase encoding, and a gradient magnetic field Gr for reading. The gradient magnetic field power supply 3 supplies the electric current to the gradient coil 2.

The couch 4 includes a couchtop 4a on which the subject P is placed. Under the control of the couch control unit 5, the couchtop 4a is inserted into a cavity (imaging port) of the gradient coil 2 in a state in which the subject P is placed thereon. Typically, the couch 4 is arranged so that the longitudinal direction thereof is parallel with the center axis of the static magnetic field magnet 1. Under the control of the calculator 20, the couch control unit 5 drives the couch 4 to move the couchtop 4a in the longitudinal direction and the vertical direction.

The transmission coil 6 is arranged inside the gradient coil 2, receives RF pulses supplied from the transmission unit 7, and generates a high-frequency magnetic field. The transmission unit 7 supplies, to the transmission coil 6, the RF pulses corresponding to the Larmor frequency determined from magnetic field intensity and a type of an atom as the target.

The reception coil 8 is arranged inside the gradient coil 2, and receives a magnetic resonance signal (hereinafter, appropriately referred to as an "MR signal") generated from the subject P due to an influence of the high-frequency magnetic field. After receiving the MR signal, the reception coil 8 outputs the received MR signal to the reception unit 9.

The transmission coil 6 and the reception coil 8 described above are merely an example. The coil may be configured by combining one or more of a coil having only a transmission function, a coil having only a reception function, and a coil having transmission and reception functions.

The reception unit 9 detects the MR signal output from the reception coil 8, and generates MR data based on the detected MR signal. Specifically, the reception unit 9 digitally converts the MR signal output from the reception coil 8 to generate the MR data. The reception unit 9 then transmits the generated MR data to the sequence control unit 10. The reception unit 9 may be provided to a platform device including the static magnetic field magnet 1, the gradient coil 2, and the like.

The sequence control unit 10 drives the gradient magnetic field power supply 3, the transmission unit 7, and the reception unit 9 to perform imaging of the subject P based on sequence information transmitted from the calculator 20. In this case, the sequence information is information for defining a procedure of performing imaging. The sequence information defines intensity of the electric current supplied from the gradient magnetic field power supply 3 to the gradient coil 2, timing for supplying the electric current, intensity of the RF pulses supplied from the transmission unit 7 to the transmission coil 6, timing for applying the RF pulses, timing for detecting the MR signal by the reception unit 9, and the like. Examples of the sequence control unit 10 include an integrated circuit such as an application specific integrated circuit (ASIC) and a field programmable gate array (FPGA), and an electronic circuit such as a central processing unit (CPU) and a micro processing unit (MPU).

After receiving the MR data from the reception unit 9 as a result of imaging the subject P by driving the gradient magnetic field power supply 3, the transmission unit 7, and the reception unit 9, the sequence control unit 10 transfers the received MR data to the calculator 20.

The calculator 20 performs overall control of the MRI apparatus 100 and generates an image, for example. The calculator 20 includes an interface unit 21, an image generation unit 22, a storage unit 23, an input unit 24, a display unit 25, and a control unit 26.

The interface unit 21 transmits the sequence information to the sequence control unit 10, and receives the MR data from the sequence control unit 10. When receiving the MR data, the interface unit 21 causes the received MR data to be stored in the storage unit 23. The MR data stored in the storage unit 23 is arranged in a k-space by the control unit 26. As a result, the storage unit 23 stores therein k-space data.

The image generation unit 22 reads out the k-space data from the storage unit 23, and performs reconstruction processing such as Fourier transformation on the read-out k-space data to generate the image.

The storage unit 23 stores therein the MR data received by the interface unit 21, the k-space data arranged in the k-space by the control unit 26, image data generated by the image generation unit 22, and the like. The storage unit 23 also stores therein a sectional position definition information table 23a. The sectional position definition information table 23a will be described later. Examples of the storage unit 23 include a semiconductor memory element such as a random access memory (RAM) and a flash memory, a hard disk, and an optical disc.

The input unit 24 receives various instructions and information input from an operator. Examples of the input unit 24 include a pointing device such as a mouse and a trackball, and an input device such as a keyboard. Under the control of the control unit 26, the display unit 25 displays various graphical user interfaces (GUIs), the image generated by the image generation unit 22, and the like. Examples of the display unit 25 include a display device for various displays such as a liquid crystal display.

The control unit 26 performs overall control of the MRI apparatus 100, and controls imaging, generation of the image, display of the image, and the like. For example, the control unit 26 receives an imaging condition input on the GUI, generates the sequence information according to the received imaging condition, and transmits the generated sequence information to the sequence control unit 10. Examples of the control unit 26 include an integrated circuit such as the ASIC and the FPGA, and an electronic circuit such as the CPU and the MPU. As described later, the control unit 26 includes components for causing a user to easily change the sectional position of the reference cross-sectional image.

The following describes an outline of processing performed by the MRI apparatus 100 according to the first embodiment. For example, the MRI apparatus 100 collects a multi-slice image in preparation scanning before collecting the reference cross-sectional image in imaging scanning, causes the multi-slice image to be stored in the storage unit 23, and automatically detects sectional positions of a plurality of reference cross-sectional images from the multi-slice image. More specifically, the MRI apparatus 100 automatically detects a characteristic portion related to a target portion (target) from the multi-slice image, and automatically detects the sectional position by calculating the sectional position using the position of the characteristic portion that is automatically detected. That is, the sectional position is defined based on the position of the characteristic portion. The imaging scanning is, for example, imaging for collecting images to be mainly used for diagnosis (also referred to as "main imaging", for example), and the preparation scanning is, for example, imaging that is typically performed before the imaging scanning (also referred to as "preparation imaging", for example).

The multi-slice image is data including a plurality of slice images collected in a 2D sequence. The multi-slice image is an example of three-dimensional data. In place of the multi-slice image, volume data collected in a 3D sequence can be used. The 2D sequence herein means a pulse sequence for collecting a two-dimensional cross-sectional image by performing encoding in a phase encoding direction and a read-out direction for one or more positions along a slice direction. The 3D sequence means a pulse sequence for collecting three-dimensional volume data by performing encoding in the slice direction in addition to the phase encoding direction and the read-out direction. The 2D sequence and the 3D sequence described above may be a radial scan sequence for collecting in the read-out direction at various angles.

Figure 2:
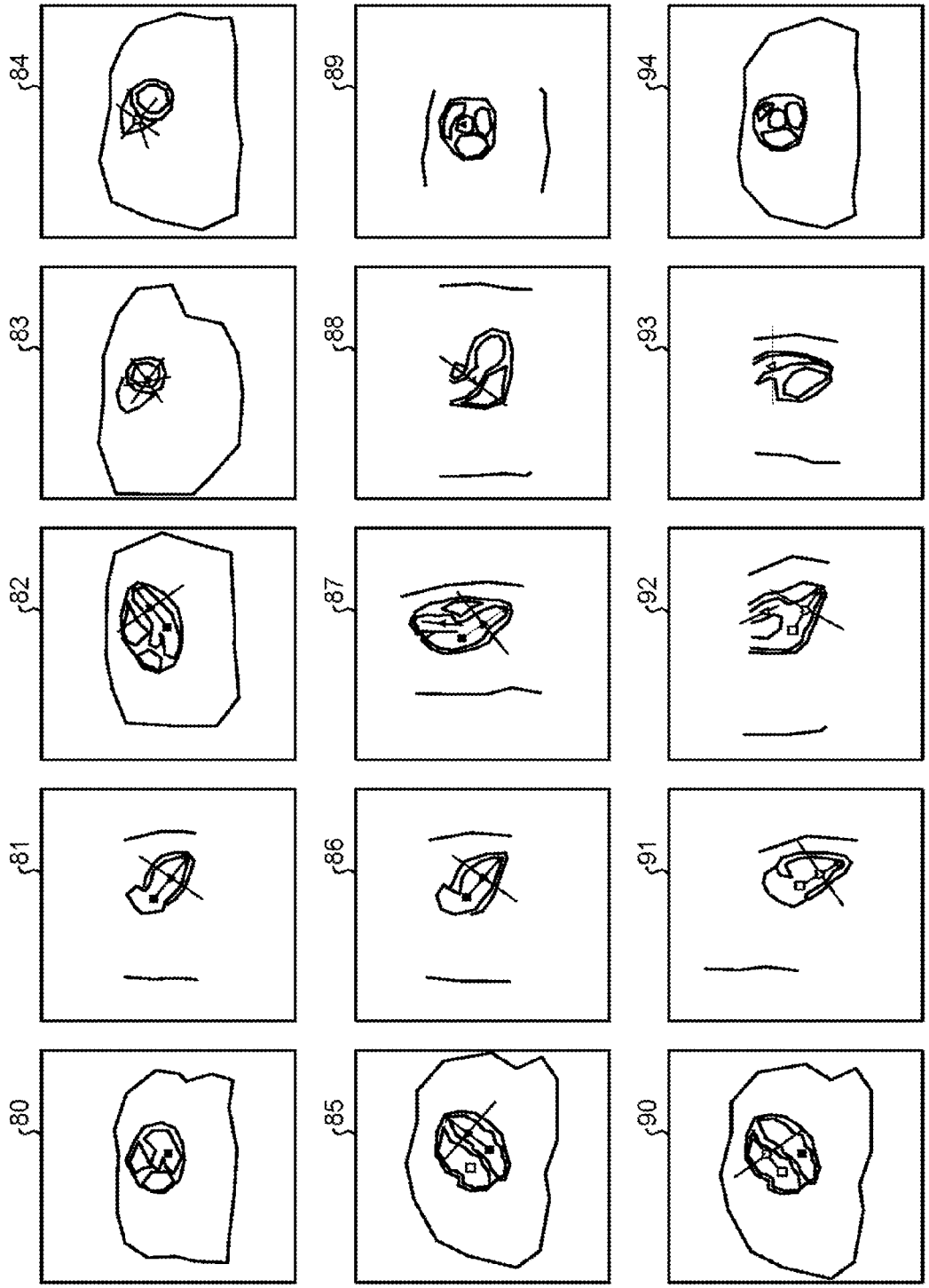
FIG. 2 is a diagram illustrating an example of a plurality of reference cross-sectional images displayed in a display region of a display unit according to the first embodiment.

The MRI apparatus 100 then generates, from the multi-slice image, the reference cross-sectional image corresponding to the automatically-detected sectional positions. The following describes an example of a case in which the multi-slice image is data including the "heart" as the target portion. The MRI apparatus 100 causes the display unit 25 to display the generated reference cross-sectional images being arranged side by side. FIG. 2 is a diagram illustrating an example of the reference cross-sectional images displayed in a display region of the display unit 25 according to the first embodiment. For example, as illustrated in the example of FIG. 2, the MRI apparatus 100 causes a transverse cross-sectional image 80, a left ventricular vertical long-axis image 81, a left ventricular horizontal long-axis image 82, a left ventricular short-axis image 83, and a right ventricular short-axis image 84 to be displayed from the left to the right in the first column from the top of the display region of the display unit 25. The MRI apparatus 100 causes a left ventricular 4-chamber long-axis image 85, a left ventricular 2-chamber long-axis image 86, a left ventricular 3-chamber long-axis image 87, a left ventricular outflow tract image 88, and an aorta valve image 89 to be displayed from the left to the right in the second column from the top of the display region of the display unit 25. The MRI apparatus 100 causes a right ventricular 4-chamber long-axis image 90, a right ventricular 2-chamber long-axis image 91, a right ventricular 3-chamber long-axis image 92, a right ventricular outflow tract image 93, and a pulmonary valve image 94 to be displayed from the left to the right in the third column from the top of the display region of the display unit 25. The images denoted by reference numerals "81" to "94" are reference cross-sectional images, and the image denoted by the reference numeral "80" is one slice image included in the multi-slice image. Hereinafter, each of the reference cross-sectional images denoted by the reference numerals "81" to "94" may be simply referred to as the "reference cross-sectional image". Hereinafter, the slice image denoted by the reference numeral "80" may also be simply referred to as the "slice image".

In the example of FIG. 2, marks indicating positions of characteristic portions of the heart are superimposed on the slice image 80 and the reference cross-sectional images 81 to 94. In the example of FIG. 2, a black quadrangle mark, a black heart mark, a black star mark, a black triangle mark, a white quadrangle mark, a white heart mark, a white star mark, and a white triangle mark illustrated in the slice image 80 and the reference cross-sectional images 81 to 94 are information indicating the positions of the characteristic portions for defining the respective sectional positions of the slice image 80 and the reference cross-sectional images 81 to 94. For example, the black quadrangle mark is the information indicating the position of a mitral valve of the heart. The black star mark is the information indicating the position of a left ventricular apex of the heart. The black heart mark is the information indicating the center position of a left ventricle (center of the left ventricle), which is the middle point between the positions of the mitral valve and the left ventricular apex of the heart. The white quadrangle mark is the information indicating the position of a tricuspid valve of the heart. The white star mark is the information indicating the position of the right ventricular apex of the heart. The white heart mark is the information indicating the center position of a right ventricle (center of the right ventricle), which is the middle point between the positions of the tricuspid valve and the right ventricular apex of the heart. The white triangle mark is the information indicating the position of a right ventricular outflow tract of the heart. These marks are also an example of the information indicating the positions of the characteristic portions. In the example of FIG. 2, all of the reference cross-sectional images 81 to 94 include the mark corresponding to the characteristic portion. However, it is sufficient that at least one of the reference cross-sectional images 81 to 94 includes the mark corresponding to the characteristic portion.

In the example of FIG. 2, for example, the sectional position of the left ventricular vertical long-axis image 81 is a sectional position passing through the position of the mitral valve and the position of the left ventricular apex of the heart, and being parallel with a head-foot direction. That is, the sectional position of the left ventricular vertical long-axis image 81 is defined based on the position of the characteristic portion such as the mitral valve and the left ventricular apex of the heart. In the example of FIG. 2, the black quadrangle mark indicating the position of the mitral valve, the black star mark indicating the position of the left ventricular apex of the heart, and the black heart mark indicating the position of the center of the left ventricle are superimposed on the left ventricular vertical long-axis image 81. Similarly, also on the other reference cross-sectional images 82 to 94 and the slice image 80, the marks indicating the positions of the characteristic portions that define the sectional position are superimposed.

In the example of FIG. 2, on each of the reference cross-sectional images 81 to 94, superimposed is a mark of a crossing line indicating the position at which the sectional position of the reference cross-sectional image of itself crosses the sectional position of the other cross-sectional image.

In this case, in each of the reference cross-sectional images 81 to 94, the user can change the position of the characteristic portion. The following describes an example of a method of changing the position of the characteristic portion by the user. For example, in each of the reference cross-sectional images 81 to 94 displayed on the display unit 25, the user can designate and change the position of the characteristic portion that defines the sectional position of the reference cross-sectional image. More specifically, in each of the reference cross-sectional images 81 to 94, the user can designate the mark indicating the position of the characteristic portion that defines the sectional position of the reference cross-sectional image and change the position of the designated mark to change the position of the characteristic portion. Designating the mark is synonymous with selecting the mark.

Figure 3:
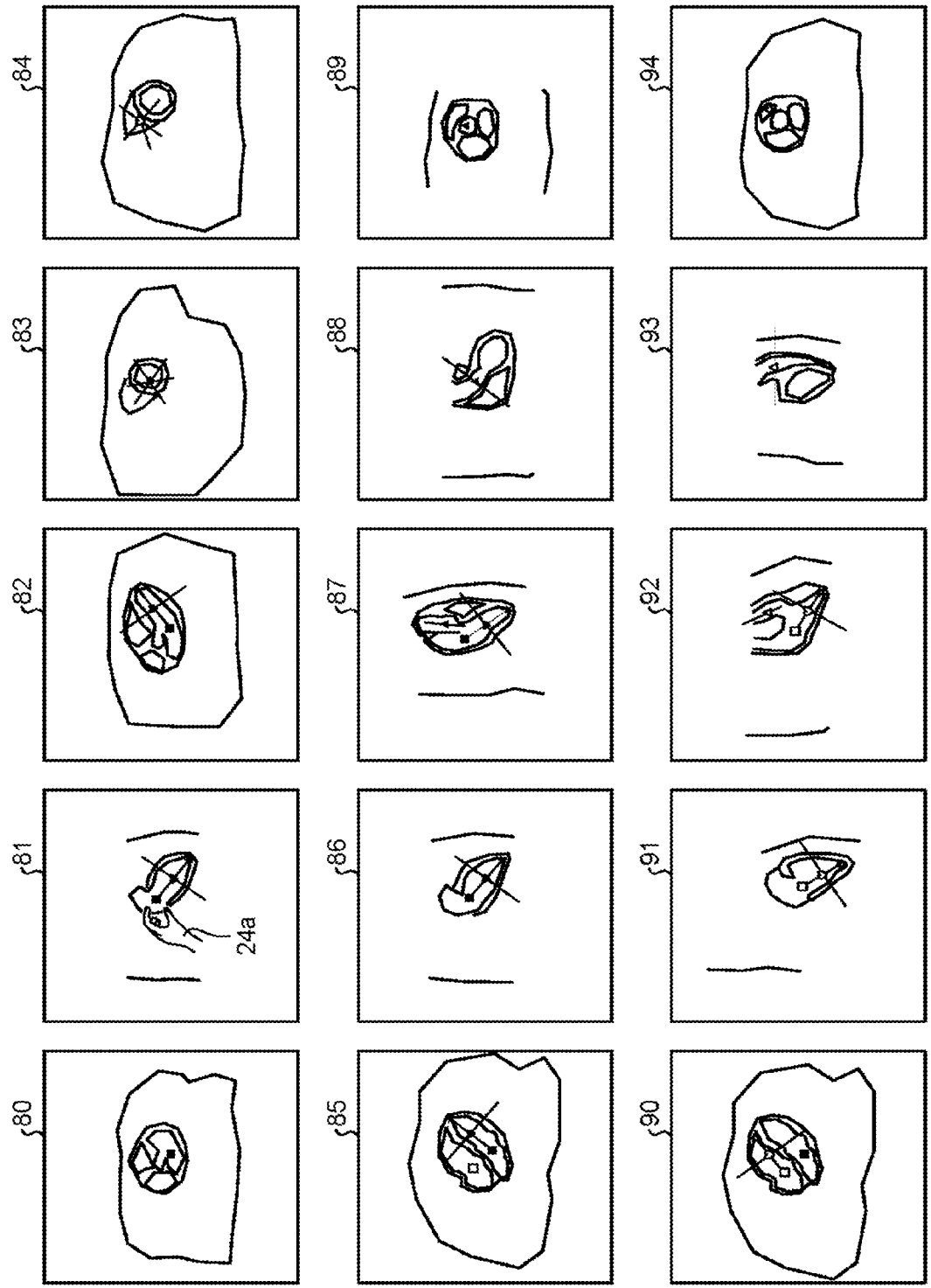
FIG. 3 is a diagram for explaining an example of a case in which, when a position of a characteristic portion is changed in a certain reference cross-sectional image, a sectional position of another reference cross-sectional image is changed in the first embodiment.

When the position of the characteristic portion is changed in a certain reference cross-sectional image, the sectional position of another reference cross-sectional image may be changed. Such a case will be described with reference to FIG. 3. FIG. 3 is a diagram for explaining an example of a case in which, when the position of the characteristic portion is changed in a certain reference cross-sectional image, the sectional position of another reference cross-sectional image is changed in the first embodiment. In the example of FIG. 3, the user operates a mouse serving as the input unit 24 to designate the black quadrangle mark to designate the mitral valve by clicking the mouse in a state in which a pointer 24a is set to the black quadrangle mark on the left ventricular vertical long-axis image 81, and thereafter, moves the pointer 24a to change the position of the black quadrangle mark. In this way, when the position of the mark indicating the position of the mitral valve is changed in the left ventricular vertical long-axis image 81, the sectional positions are changed in six reference cross-sectional images including the left ventricular horizontal long-axis image 82, the left ventricular short-axis image 83, the left ventricular 4-chamber long-axis image 85, the left ventricular 2-chamber long-axis image 86, the left ventricular 3-chamber long-axis image 87, and the right ventricular 4-chamber long-axis image 90 the sectional positions of which are defined using the position of the mitral valve, and the six reference cross-sectional images after the sectional positions are changed are displayed as illustrated in the example of FIG. 3. However, in this case, the number of the displayed reference cross-sectional images (in the example of FIG. 3, the number of the reference cross-sectional images is "14") is large, so that, when the position of the mark indicating the position of the mitral valve is changed in the left ventricular vertical long-axis image 81, the user cannot easily grasp the reference cross-sectional image in which the sectional position is changed among the other reference cross-sectional images 82 to 94.

For this reason, when the mark indicating the position of the characteristic portion of the target the position of which is to be changed is designated and the position of the designated mark is changed in a certain reference cross-sectional image, the MRI apparatus 100 according to the embodiment causes another reference cross-sectional image the sectional position of which is defined using the characteristic portion the position of which is indicated by the mark the position of which is changed to be emphasized as compared with the rest of the reference cross-sectional images other than the certain reference cross-sectional image and the other reference cross-sectional image. For example, the MRI apparatus 100 can be configured not to perform emphasis when the mark is not designated.

Figure 4:
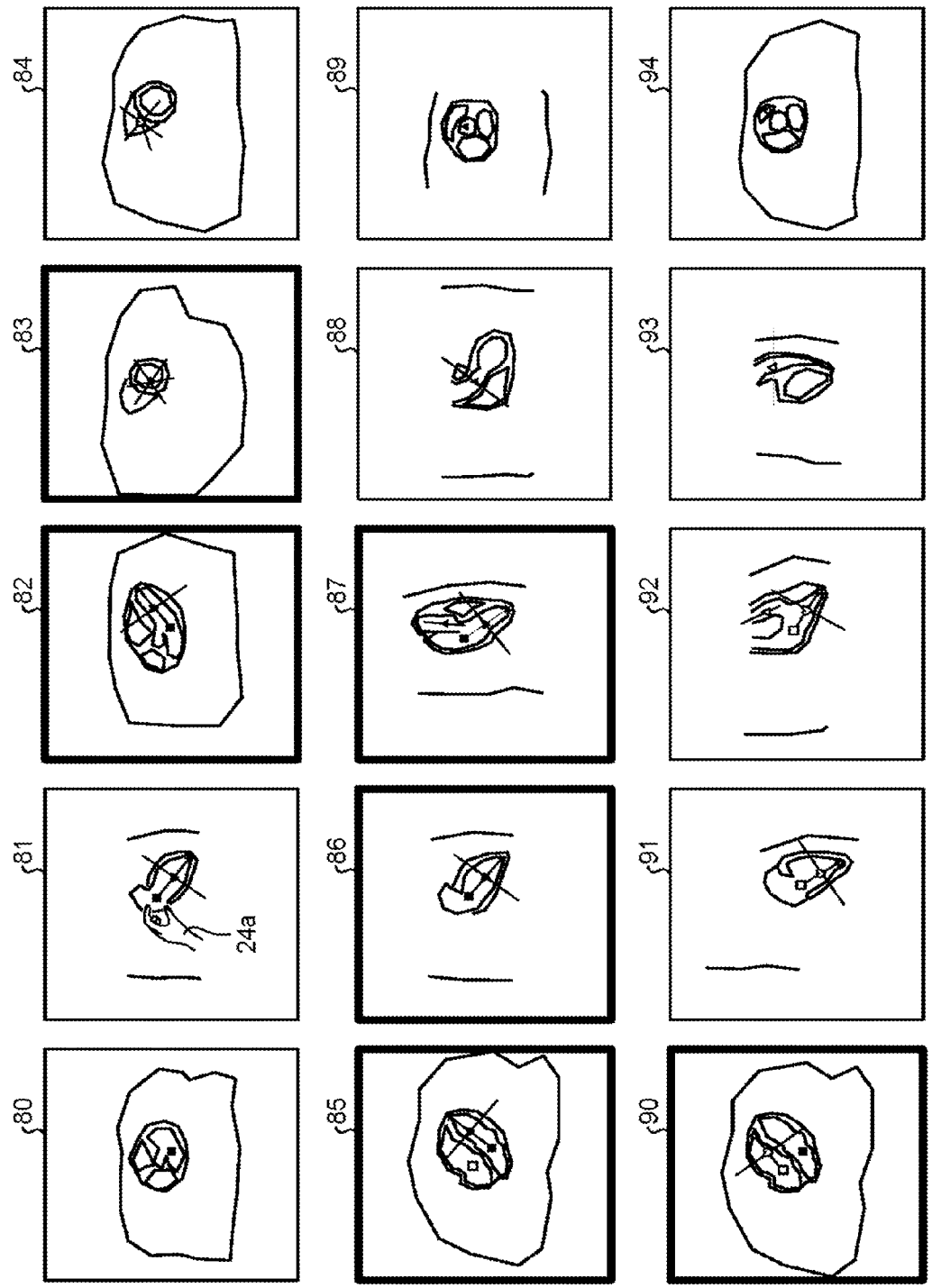
FIG. 4 is a diagram for explaining an example of a case in which the reference cross-sectional image is emphasized according to the first embodiment.

FIG. 4 is a diagram for explaining an example of a case in which the reference cross-sectional image is emphasized according to the first embodiment. For example, when the position of the mark indicating the position of the mitral valve is changed in the left ventricular vertical long-axis image 81 as illustrated in the example of FIG. 3, the MRI apparatus 100 causes, as illustrated in the example of FIG. 4, the six reference cross-sectional images including the left ventricular horizontal long-axis image 82, the left ventricular short-axis image 83, the left ventricular 4-chamber long-axis image 85, the left ventricular 2-chamber long-axis image 86, the left ventricular 3-chamber long-axis image 87, and the right ventricular 4-chamber long-axis image 90 to be emphasized as compared with the reference cross-sectional images 81, 84, 88, and 91 to 94 other than the six reference cross-sectional images. In the example of FIG. 4, as an example of emphasis, the six reference cross-sectional images are emphasized with the frames thereof thickened. In this way, when the mark indicating the position of the characteristic portion of the target the position of which is to be changed is designated in a certain reference cross-sectional image and the position of the designated mark is changed, the MRI apparatus 100 causes the other reference cross-sectional images to be emphasized the sectional position of which is changed due to the change of the position of the characteristic portion indicated by the designated mark. Accordingly, with the MRI apparatus 100, the user can easily grasp the reference cross-sectional image the sectional position of which is changed according to the change of the position of the mark indicating the position of the characteristic portion in a certain reference cross-sectional image. With the MRI apparatus 100, the user thus can easily perform positioning of the reference cross-sectional image.

When the positioning of the sectional positions of the reference cross-sectional images displayed on the display unit 25 is completed, the MRI apparatus 100 performs imaging scanning at the changed sectional positions.

Figure 5:
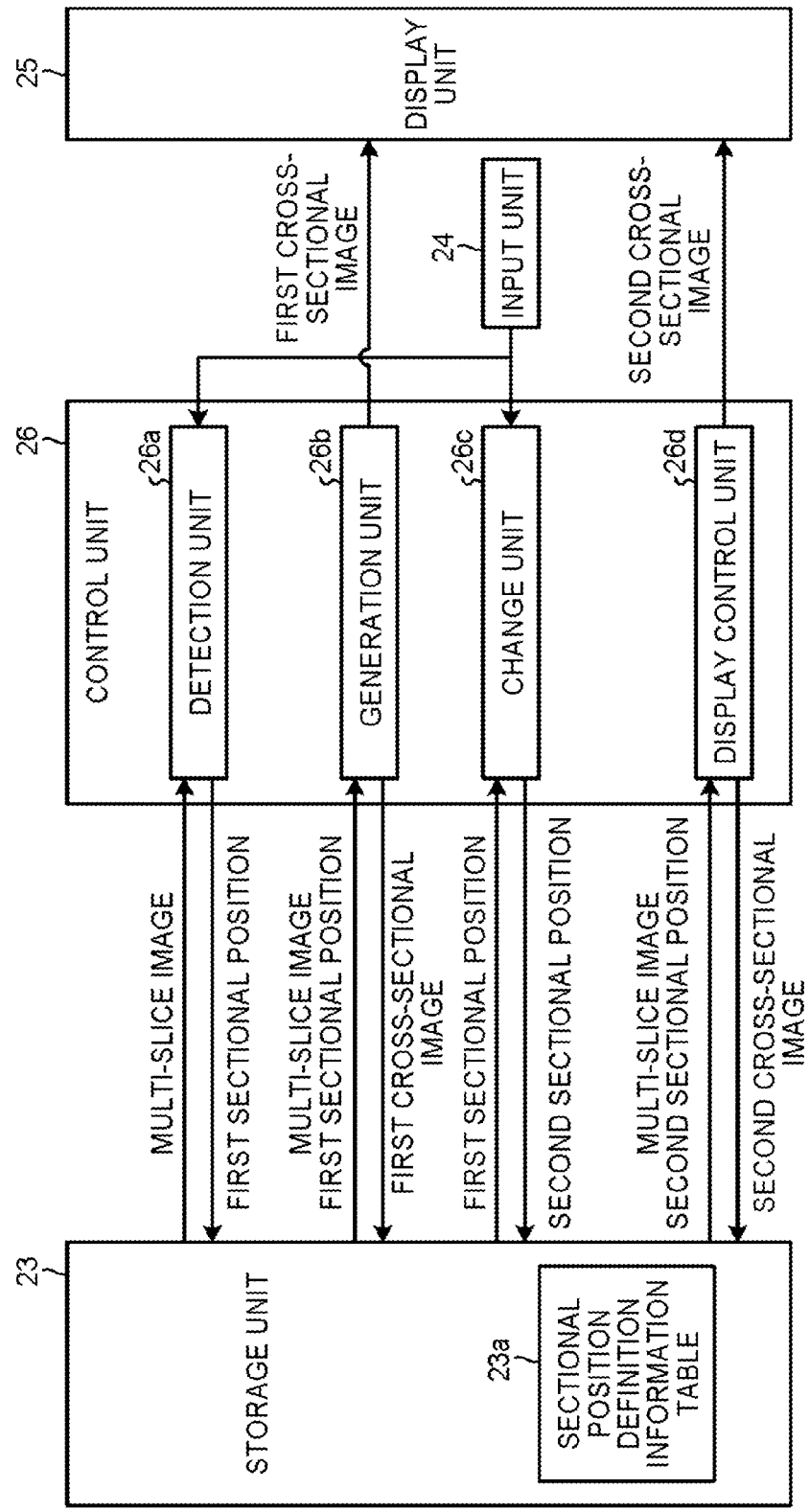
FIG. 5 is a functional block diagram illustrating an example of a control unit according to the first embodiment.

Next, the following describes an example of the control unit 26 according to the embodiment. FIG. 5 is a functional block diagram illustrating an example of the control unit 26 according to the first embodiment. As illustrated in the example of FIG. 5, the control unit 26 includes a detection unit 26a, a generation unit 26b, a change unit 26c, and a display control unit 26d.

The detection unit 26a acquires, from the storage unit 23, the multi-slice image that is collected in the preparation scanning and stored in the storage unit 23, and automatically detects the sectional positions of the reference cross-sectional images from the acquired multi-slice image. For example, the detection unit 26a detects the respective sectional positions of the reference cross-sectional images of 14 types including the left ventricular vertical long-axis image, the left ventricular horizontal long-axis image, the left ventricular short-axis image, the right ventricular short-axis image, the left ventricular 4-chamber long-axis image, the left ventricular 2-chamber long-axis image, the left ventricular 3-chamber long-axis image, the left ventricular outflow tract image, the aorta valve image, the right ventricular 4-chamber long-axis image, the right ventricular 2-chamber long-axis image, the right ventricular 3-chamber long-axis image, the right ventricular outflow tract image, and the pulmonary valve image. The detection unit 26a then causes the automatically-detected sectional positions to be stored in the storage unit 23. The sectional positions that are automatically detected by the detection unit 26a are the sectional positions of the cross-sectional images collected in the imaging scanning. Hereinafter, the sectional position that is automatically detected by the detection unit 26a may be referred to as a "first sectional position".

The generation unit 26b generates the reference cross-sectional images corresponding to a plurality of first sectional positions, and causes the display unit 25 to display the generated reference cross-sectional images. For example, the generation unit 26b first acquires the multi-slice image and the first sectional positions from the storage unit 23. The generation unit 26b then generates, from the multi-slice image, the reference cross-sectional images corresponding to the respective first sectional positions through multi-planar reconstruction (MPR) processing. Hereinafter, the reference cross-sectional image generated by the generation unit 26b may be referred to as a "first cross-sectional image". The generation unit 26b then causes the display unit 25 to display the first cross-sectional image. For example, as illustrated in the example of FIG. 2, the generation unit 26b causes the display unit 25 to display the transverse cross-sectional image 80 and the first cross-sectional images 81 to 94 on which the various marks described above are superimposed. The generation unit 26b causes the first cross-sectional image to be stored in the storage unit 23.

When the position of the mark is changed by the user in a certain first cross-sectional image, the change unit 26c calculates the sectional position of another first cross-sectional image the sectional position of which is defined using the changed position of the characteristic portion indicated by the mark the position of which is changed. The change unit 26c then causes the calculated sectional position to be stored in the storage unit 23. Hereinafter, the sectional position calculated by the change unit 26c may be referred to as a "second sectional position".

The display control unit 26d generates the reference cross-sectional image that corresponds to the second sectional position and is emphasized as compared with the other reference cross-sectional images with the frame thereof thickened, and causes the display unit 25 to display the generated reference cross-sectional image. For example, the display control unit 26d first acquires the multi-slice image and the second sectional position from the storage unit 23. The display control unit 26d then generates, from the multi-slice image, the reference cross-sectional image corresponding to the second sectional position through the MPR processing. At this point, the display control unit 26d generates the reference cross-sectional image that is emphasized with the frame thereof thickened, for example. Hereinafter, the reference cross-sectional image generated by the display control unit 26d may be referred to as a "second cross-sectional image". The display control unit 26d then causes the display unit 25 to display the second cross-sectional image. The display control unit 26d controls the generated second cross-sectional image to be stored in the storage unit 23.

Figure 6:
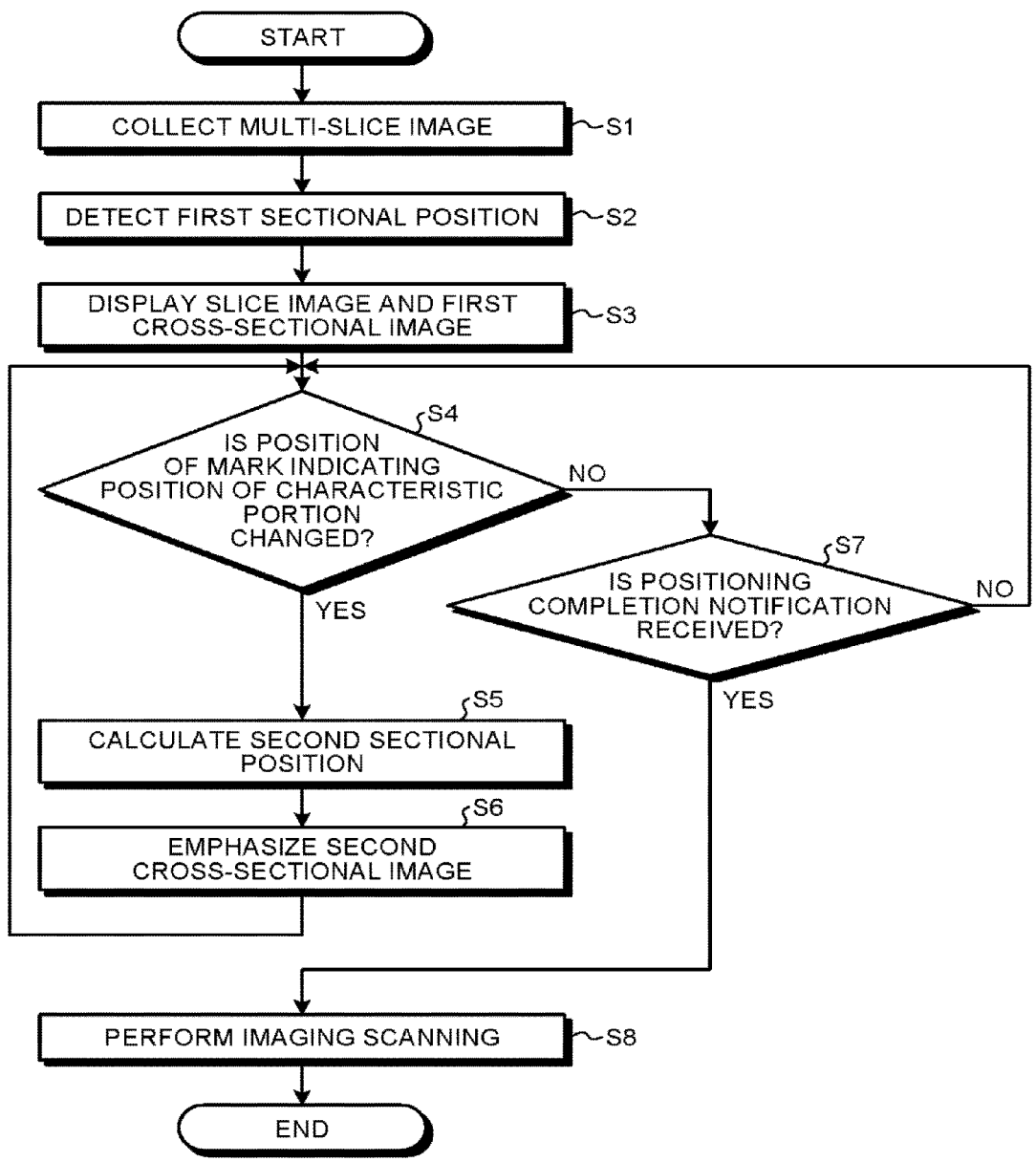
FIG. 6 is a flowchart illustrating a processing procedure according to the first embodiment.

Next, the following describes a processing procedure performed by the MRI apparatus 100 according to the embodiment. FIG. 6 is a flowchart illustrating the processing procedure in the first embodiment. In the first embodiment, assumed is a test using 14 types of reference cross-sectional images including the left ventricular vertical long-axis image, the left ventricular horizontal long-axis image, the left ventricular short-axis image, the right ventricular short-axis image, the left ventricular 4-chamber long-axis image, the left ventricular 2-chamber long-axis image, the left ventricular 3-chamber long-axis image, the left ventricular outflow tract image, the aorta valve image, the right ventricular 4-chamber long-axis image, the right ventricular 2-chamber long-axis image, the right ventricular 3-chamber long-axis image, the right ventricular outflow tract image, and the pulmonary valve image.

As illustrated in the example of FIG. 6, the sequence control unit 10 drives the gradient magnetic field power supply 3, the transmission unit 7, and the reception unit 9 of the MRI apparatus 100 to collect the multi-slice image (Step S1). According to the embodiment, for example, the multi-slice image includes a plurality of transverse cross-sectional images. The multi-slice image also includes the heart. The heart is an example of the target portion. While performing electro cardio gram (ECG) synchronization, the sequence control unit 10 drives the gradient magnetic field power supply 3, the transmission unit 7, and the reception unit 9 of the MRI apparatus 100 so that a collection timing is limited to a diastole phase and the MR data of the multi-slice image is collected under breath-holding, for example. To collect the MR data of the multi-slice image, the sequence control unit 10 uses, for example, 2D fast field echo (FFE) or 2D steady-state free precession (SSFP). The sequence control unit 10 transmits the collected MR data to the image generation unit 22 via the interface unit 21. When receiving the MR data, the image generation unit 22 generates the multi-slice image using the received MR data, and causes the generated multi-slice image stored in the storage unit 23. The multi-slice image may include a plurality of sagittal cross-sectional images or coronal cross-sectional images.

Next, the detection unit 26a detects (automatically detects) the sectional positions (first sectional positions) of the reference cross-sectional images of 14 types described above (Step S2). The following describes the sectional position. The sectional position means, for example, a position representing a plane in a three-dimensional image space, and is represented with a plurality of parameters. In the following description, each of these parameters is referred to as a "position parameter". As represented by the following expressions (1) and (2), for example, the position parameter is represented with a center coordinate point o and two unit vectors u and v orthogonal to each other.

$$o=(o_x,o_y,o_z) \quad (1)$$

$$u=(u_x,u_y,u_z),\ v=(v_x,v_y,v_z) \quad (2)$$

To detect the sectional position means to obtain the position parameters o, u, and v. The detection unit 26a causes the position parameters for each of the detected reference cross-sectional images to be stored in the storage unit 23. A method of representing the position parameters is not limited to the method described above. For example, the position parameters may be represented in a three-dimensional device space that is determined based on the center of the magnetic field of the MRI apparatus 100, the longitudinal direction of the couch, and the like in place of the three-dimensional image space, or may be represented with three coordinate points in place of the center coordinate point and the two unit vectors orthogonal to each other. That is, any method can be used so long as the sectional position is geometrically and uniquely determined.

For example, the detection unit 26a automatically detects the position of the characteristic portion in the multi-slice image by performing template matching with the multi-slice image using templates of surrounding image patterns of the characteristic portions of the heart such as the mitral valve, the tricuspid valve, the aorta valve, the pulmonary valve, the left/right ventricular apex of the heart, the left/right ventricular outflow tract, and an anterior wall of left/right ventricle, and calculates the position parameters of the reference cross-sectional images based on the detected characteristic portions. In this case, the templates as described above are assumed to be generated in advance before the template matching is performed. For example, the sectional position of the left ventricular 4-chamber long-axis image as one of the reference cross-sectional images is a plane passing through the position m of the mitral valve, the position t of the tricuspid valve, and the position a of the left ventricular apex of the heart. That is, the sectional position of the left ventricular 4-chamber long-axis image is defined with three positions including the position m of the mitral valve, the position t of the tricuspid valve, and the position a of the left ventricular apex of the heart. In this case, when the position m of the mitral valve, the position t of the tricuspid valve, and the position a of the left ventricular apex of the heart are represented by the following expression (3), the position parameters o, u, and v indicating the sectional position of the left ventricular 4-chamber long-axis image can be represented by the following expression (4).

$$m=(m_x,m_y,m_z),\ t=(t_x,t_y,t_z),\ a=(a_x,a_y,a_z) \quad (3)$$

$$o=(m+a)/2,\ v'=a-m,\ v=v'/|v'|,\ u'=((t-m)\times v)\times v,\ u=u'/|u'| \quad (4)$$

In the expression (4), "(t−m)×v" means a cross product of the vector (t−m) and the vector v, and "((t−m)×v)×v" means the cross product of the vector ((t−m)×v) and the vector v.

A method of detecting the sectional position of the reference cross-sectional image is not limited to the template matching. For example, the detection unit 26a may construct a discriminator in advance through machine learning from the surrounding image patterns of the characteristic portions of the heart, and may automatically detect the positions of the characteristic portions in the multi-slice image using this discriminator. The detection unit 26a can detect the sectional position of the reference cross-sectional image by receiving the positions of the characteristic portions of the heart input by the operator via the input unit 24. However, this operation is very complicated and time-consuming, so that the method of automatically detecting sectional positions of the reference cross-sectional images is typically preferred.

Next, the generation unit 26b acquires the multi-slice image from the storage unit 23, generates the reference cross-sectional image (first cross-sectional image) corresponding to each of the first sectional positions from the multi-slice image through the MPR processing, and causes the display unit 25 to display the first cross-sectional image together with the slice image (Step S3). For example, the generation unit 26b causes the display unit 25 to display the first cross-sectional images and the slice image on which the various marks are superimposed. The generation unit 26b causes the first cross-sectional image to be stored in the storage unit 23. That is, the generation unit 26b generates the first cross-sectional images as the localizer images for setting the sectional position of main imaging based on the characteristic portion of the target portion detected from the three-dimensional data including the target portion. The generation unit 26b then lists the generated first cross-sectional images on the display unit 25. The generation unit 26b causes the mark corresponding to the characteristic portion to be displayed in a superimposed manner on at least one of the first cross-sectional images.

Next, the change unit 26c determines whether the user changes the position of the mark via the input unit 24 (Step S4). That is, the change unit 26c determines whether the setting operation of the sectional position is received.

If the change unit 26c determines that the user changes the position of the mark via the input unit 24 (Yes at Step S4), that is, if the change unit 26c receives the setting operation of the sectional position, the change unit 26c newly calculates the sectional position (second sectional position) using the changed position of the characteristic portion indicated by the mark the position of which is changed, for the reference cross-sectional image the sectional position of which is defined using the position of the characteristic portion indicated by the mark the position of which is changed (Step S5). For example, the change unit 26c calculates a three-dimensional position in the three-dimensional image space from the changed two-dimensional position of the mark on the reference cross-sectional image on which the position of the mark is changed. The change unit 26c then refers to the sectional position definition information table 23a, and specifies another reference cross-sectional image the sectional position of which is defined using the position of the characteristic portion indicated by the mark the position of which is changed.

The following describes the sectional position definition information table 23a. The sectional position definition information table 23a is a table in which the reference cross-sectional image and the characteristic portion that defines the sectional position of the reference cross-sectional image are registered in an associated manner. That is, the reference cross-sectional image is defined to pass through a plurality of characteristic portions. Alternatively, the reference cross-sectional image is defined to pass through points obtained with the characteristic portions. Alternatively, the reference cross-sectional image is defined to pass through the points obtained with one characteristic portion and the other characteristic portion. FIG. 7 is a diagram illustrating an example of a data structure of the sectional position definition information table 23a according to the first embodiment. The sectional position definition information table 23a illustrated in the example of FIG. 7 includes items of "ID (Identification)" and "definition parameter". In the item of "ID", identification information indicating the type of the reference cross-sectional image is registered. In the item of "definition parameter", registered is the characteristic portion that defines the sectional position of the reference cross-sectional image of the type indicated by the identification information registered in the item of "ID", or information indicating a conversion expression from the characteristic portion to the position parameter. The first record of the sectional position definition information table 23a in the example of FIG. 7 represents that the sectional position of the left ventricular 4-chamber long-axis image indicated by the identification information "L4CH" is defined with three positions including the position of the mitral valve, the position of the tricuspid valve, and the position of the left ventricular apex of the heart.

For example, when the characteristic portion the position of which is indicated by the mark the position of which is changed is the mitral valve, the change unit 26c refers to the sectional position definition information table 23a and specifies the record in which the mitral valve is registered in the item of "definition parameter". The change unit 26c then specifies the identification information registered in the item of "ID" in the specified record. The change unit 26c then specifies the reference cross-sectional image of the type indicated by the specified identification information to specify another reference cross-sectional image the sectional position of which is defined using the position of the characteristic portion indicated by the mark the position of which is changed.

The sectional position definition information table 23a is not limited to a table having the data structure illustrated in the example of FIG. 7. The sectional position definition information table 23a may have any data structure so long as information associating the reference cross-sectional image with the characteristic portion that defines the sectional position of the reference cross-sectional image is registered therein.

The change unit 26c calculates the changed sectional position by calculating the changed position parameter using the same expression as the expression (4) based on the calculated three-dimensional position for the reference cross-sectional image the sectional position of which is defined using the position of the characteristic portion indicated by the mark the position of which is changed.

The following describes a case in which, in the example of FIG. 2, the user changes the position of the mark indicating the position of the mitral valve in the left ventricular vertical long-axis image 81. In this case, the change unit 26c calculates the three-dimensional position in the three-dimensional space from the two-dimensional position of the changed mark (the two-dimensional position of the black quadrangle mark) on the left ventricular vertical long-axis image 81. The change unit 26c then calculates the changed sectional position by calculating the changed position parameter using the same expression as the expression (4) for each of the left ventricular horizontal long-axis image 82, the left ventricular short-axis image 83, the left ventricular 4-chamber long-axis image 85, the left ventricular 2-chamber long-axis image 86, the left ventricular 3-chamber long-axis image 87, and the right ventricular 4-chamber long-axis image 90 the sectional positions of which are defined using the position of the mitral valve indicated by the mark.

The following describes a case in which, in the example of FIG. 2, the user changes the position of the mark indicating the position of the right ventricular outflow tract in the right ventricular 3-chamber long-axis image 92. In this case, the change unit 26c calculates the three-dimensional position in the three-dimensional space from the two-dimensional position of the changed mark (white triangle mark) on the right ventricular 3-chamber long-axis image 92. The change unit 26c then calculates the changed sectional position by calculating the changed position parameter using the same expression as the expression (4) for each of the right ventricular outflow tract image 93 and the pulmonary valve image 94 the sectional positions of which are defined using the position of the right ventricular outflow tract indicated by the mark.

Next, the display control unit 26d generates the reference cross-sectional image (second cross-sectional image) that corresponds to the changed sectional position and is emphasized as compared with the other reference cross-sectional images with the frame thereof thickened, for example, using the changed sectional position (second sectional position), and causes the display unit 25 to emphasize the generated reference cross-sectional image (Step S6). Accordingly, the display control unit 26d can display the generated reference cross-sectional image in an emphasized manner as compared with the other reference cross-sectional images. For example, as illustrated in the example of FIG. 4, the display control unit 26d causes the display unit 25 to display six second cross-sectional images the frames of which are thickened (the left ventricular horizontal long-axis image 82, the left ventricular short-axis image 83, the left ventricular 4-chamber long-axis image 85, the left ventricular 2-chamber long-axis image 86, the left ventricular 3-chamber long-axis image 87, and the right ventricular 4-chamber long-axis image 90). As a result, the six reference cross-sectional images are displayed in an emphasized manner as compared with the reference cross-sectional images 81, 84, 88, and 91 to 94.

The process of the display control unit 26d then returns to Step S4. That is, while the position of the mark indicating the position of the characteristic portion is being changed (while a changing operation is performed via the input unit 24), the display control unit 26d controls to emphasize the reference cross-sectional image. Accordingly, while the position of the characteristic portion is being changed, the user can easily grasp the reference cross-sectional image the sectional position of which is changed according to the change of the position of the characteristic portion in a certain reference cross-sectional image. The user thus can easily perform positioning of the reference cross-sectional image. When the change of the position of the mark indicating the position of the characteristic portion is finished, the display control unit 26d cancels emphasis on the reference cross-sectional image. As described above, while the position of the mark is being changed in the setting operation, the display control unit 26d controls to emphasize the reference cross-sectional image the sectional position of which is defined using the characteristic portion corresponding to the mark among the listed reference cross-sectional image.

Even when the change of the position of the mark is finished, the display control unit 26d can continue to emphasize the reference cross-sectional image without canceling the emphasis on the reference cross-sectional image until the change unit 26c determines that the user newly changes the position of the mark indicating the position of the characteristic portion via the input unit 24. That is, not only in the period in which the position of the mark is being changed in the setting operation but also when the setting operation is finished, the display control unit 26d continues to emphasize the reference cross-sectional image the sectional position of which is defined using the characteristic portion corresponding to the mark among the listed reference cross-sectional images. In this way, by continuing to emphasize the reference cross-sectional image even after the changing operation is finished until the next changing operation is started, the user can more thoroughly confirm the changed reference cross-sectional image as compared with the case in which the emphasis on the reference cross-sectional image is canceled at the same time when the change of the position of the mark is finished. The user thus can more easily perform positioning of the reference cross-sectional image. In the above example, the emphasis is canceled taking an opportunity when the next changing operation is started. However, the embodiment is not limited thereto. The emphasis may be canceled at any other opportunities. For example, the emphasis may be canceled when a predetermined time has elapsed after the changing operation is finished.

If it is determined that the user does not change the position of the characteristic portion via the input unit 24 (No at Step S4), the change unit 26c determines whether a notification that positioning of the sectional position of the reference cross-sectional image is completed (positioning completion notification) is received from the user via the input unit 24 (Step S7). If the change unit 26c determines that the positioning completion notification is not received (No at Step S7), the process returns to Step S4 described above.

On the other hand, if it is determined that the positioning completion notification is received (Yes at Step S7), the sequence control unit 10 drives the gradient magnetic field power supply 3, the transmission unit 7, and the reception unit 9 of the MRI apparatus 100 to perform imaging scanning for collecting the cross-sectional images by using the positioned sectional positions (Step S8), and ends the process. That is, the sequence control unit 10 performs imaging scanning based on the sectional positions after the setting operation.

The MRI apparatus 100 according to the first embodiment has been described above. With the MRI apparatus 100, as described above, the user can easily perform positioning of the reference cross-sectional image.

A method of emphasizing the reference cross-sectional image in the first embodiment is not limited to the method of thickening the frame as illustrated in FIG. 4. The reference cross-sectional image as a target of emphasis and the reference cross-sectional image that is not the target of emphasis may be displayed in different display modes. For example, the type or color of the frame may be displayed in different display modes. A periphery of the frame of the reference cross-sectional image as a target of emphasis may be shadowed, or reflection of light, luster, gradation, and chamfering may be applied to the frame of the reference cross-sectional image as a target of emphasis. The reference cross-sectional image as a target of emphasis may be highlighted. The term "highlight" means, for example, a display method of reversing the background color to be displayed. To emphasize the reference cross-sectional image as a target of emphasis also includes a case in which the reference cross section as a target of emphasis is displayed on the display unit 25 and the reference cross section that is not the target of emphasis is not displayed on the display unit 25. A processing to emphasize the reference cross-sectional image as a target of emphasis also includes a processing to make the reference cross-sectional image that is not the target of emphasis inconspicuous. For example, the processing to make the reference cross-sectional image that is not the target of emphasis inconspicuous includes a processing to lower contrast of the reference cross-sectional image that is not the target of emphasis.

Figure 8:
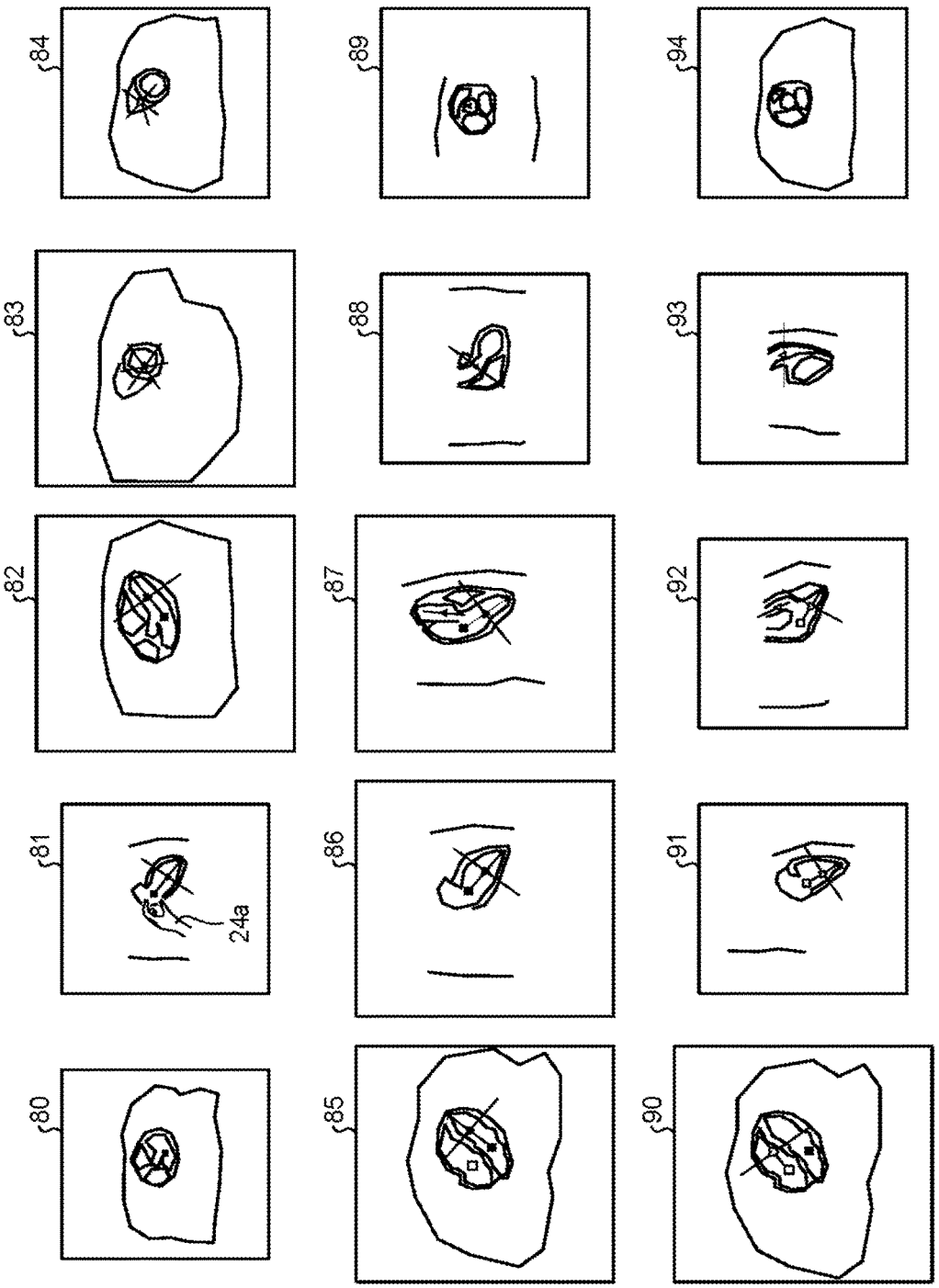
FIG. 8 is a diagram illustrating another example of a method of emphasizing the reference cross-sectional image according to the first embodiment.
Figure 9:
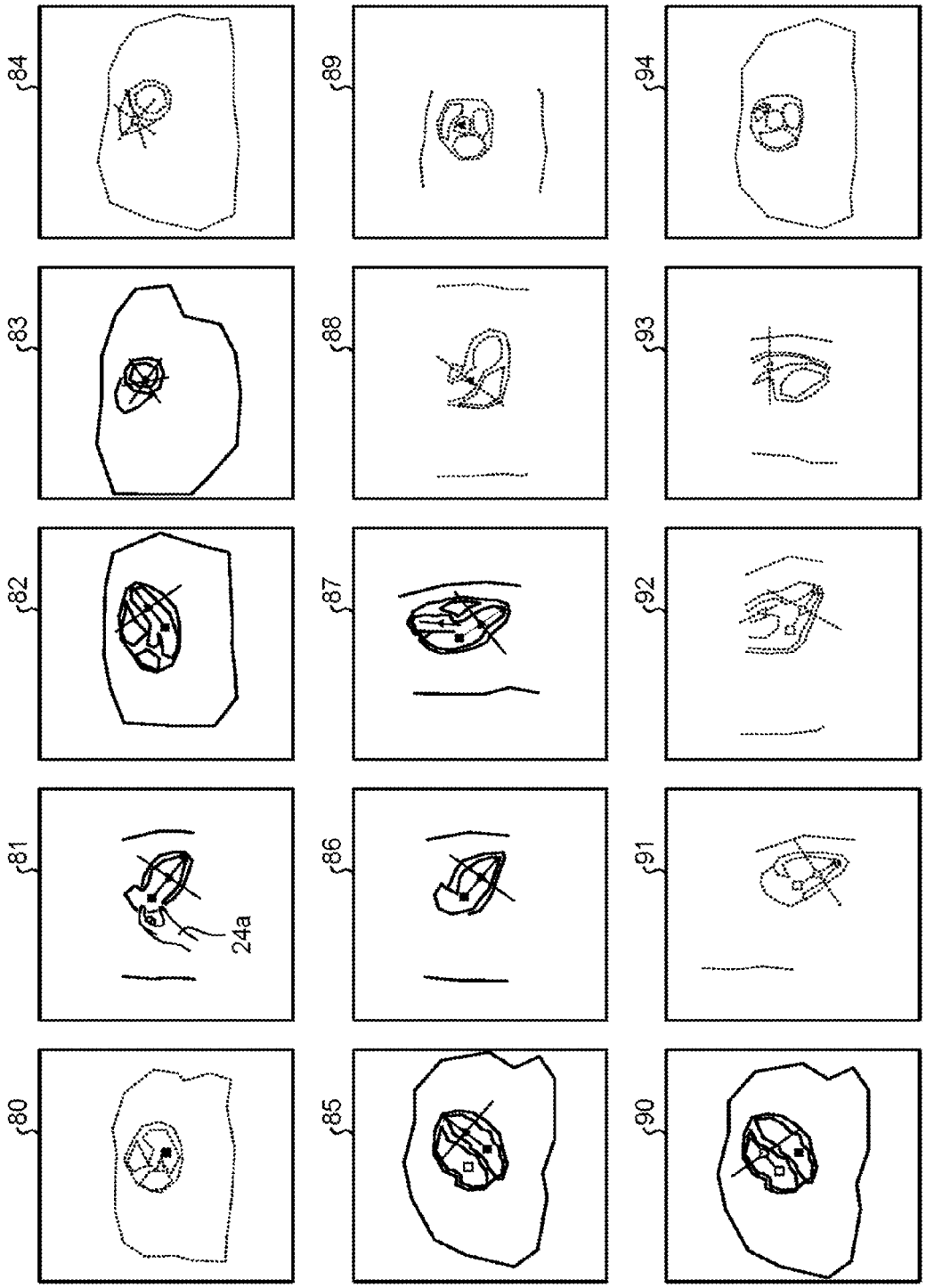
FIG. 9 is a diagram illustrating another example of the method of emphasizing the reference cross-sectional image according to the first embodiment.

FIGS. 8 and 9 are diagrams illustrating another example of the method of emphasizing the reference cross-sectional image according to the first embodiment. For example, as illustrated in the example of FIG. 8, each of the sizes of the reference cross-sectional images 80, 81, 84, 88, 89, and 91 to 94 that are not the targets of emphasis may be caused to be smaller than each of the sizes of the reference cross-sectional images 82, 83, 85 to 87, and 90 as targets of emphasis. Alternatively, as illustrated in the example of FIG. 9, contrast of the reference cross-sectional images 80, 81, 84, 88, 89, and 91 to 94 that are not the targets of emphasis may be caused to be lower than the contrast of the reference cross-sectional images 82, 83, 85 to 87, and 90 as the targets of emphasis.

First Modification of First Embodiment

In the MRI apparatus 100 according to the first embodiment described above, the second cross-sectional image is emphasized while the position of the mark indicating the position of the characteristic portion is being changed. However, the second cross-sectional image may be continuously emphasized until the positioning completion notification is received even after the position of the mark is changed. Such an embodiment will be described as a first modification of the first embodiment.

In the MRI apparatus according to the first embodiment, processing in a case in which the process returns to Step S4 from Step S6 is different from that of the MRI apparatus 100 according to the first embodiment. For this reason, the following describes an example of the processing in a case in which the process returns to Step S4 from Step S6 in the MRI apparatus according to the first modification with reference to FIGS. 10 and 11. For example, when the process returns to Step S4 from Step S6, the emphasized reference cross-sectional image (second cross-sectional image) is present on the display unit 25.

The following describes a case in which the emphasized reference cross-sectional images 82, 83, 85 to 87, and 90 are present as illustrated in the example of FIG. 4. The example of FIG. 4 represents a case in which the reference cross-sectional images 82, 83, 85 to 87, and 90 are emphasized because the position of the mark indicating the position of the mitral valve is changed in the reference cross-sectional image 81. In such a case, for example, when the position of the mark indicating the position of the characteristic portion of the reference cross-sectional image 82 is changed, it is determined that the position of the mark indicating the position of the characteristic portion is changed at Step S4, and the process proceeds to Step S5 and Step S6 again. In the MRI apparatus according to the first modification, the reference cross-sectional images that have been emphasized continue to be emphasized at Step S5 and Step S6. That is, in the MRI apparatus according to the first modification, the display control unit 26d continues to emphasize the reference cross-sectional images that have already been emphasized even after the position of the characteristic portion is changed. With the MRI apparatus according to the first modification, the user thus can take time to grasp the reference cross-sectional image the sectional position of which is changed according to the change of the position of the characteristic portion in a certain reference cross-sectional image after the operation for changing the characteristic portion is finished. Accordingly, with the MRI apparatus according to the first modification, the user can more easily perform positioning of the reference cross-sectional image.

The change unit 26c may cause the position parameters before and after the position of the characteristic portion is changed to be stored in the storage unit 23, and the display control unit 26d may acquire the position parameters stored in the storage unit 23 before and after the position of the characteristic portion is changed, and may generate and display the reference cross-sectional images before and after the position of the characteristic portion is changed using the acquired position parameters. This configuration can cause the user to confirm the reference cross-sectional images before and after the position of the characteristic portion is changed. Accordingly, for example, the user can determine whether the position of the characteristic portion has been successfully corrected.

Figure 10:
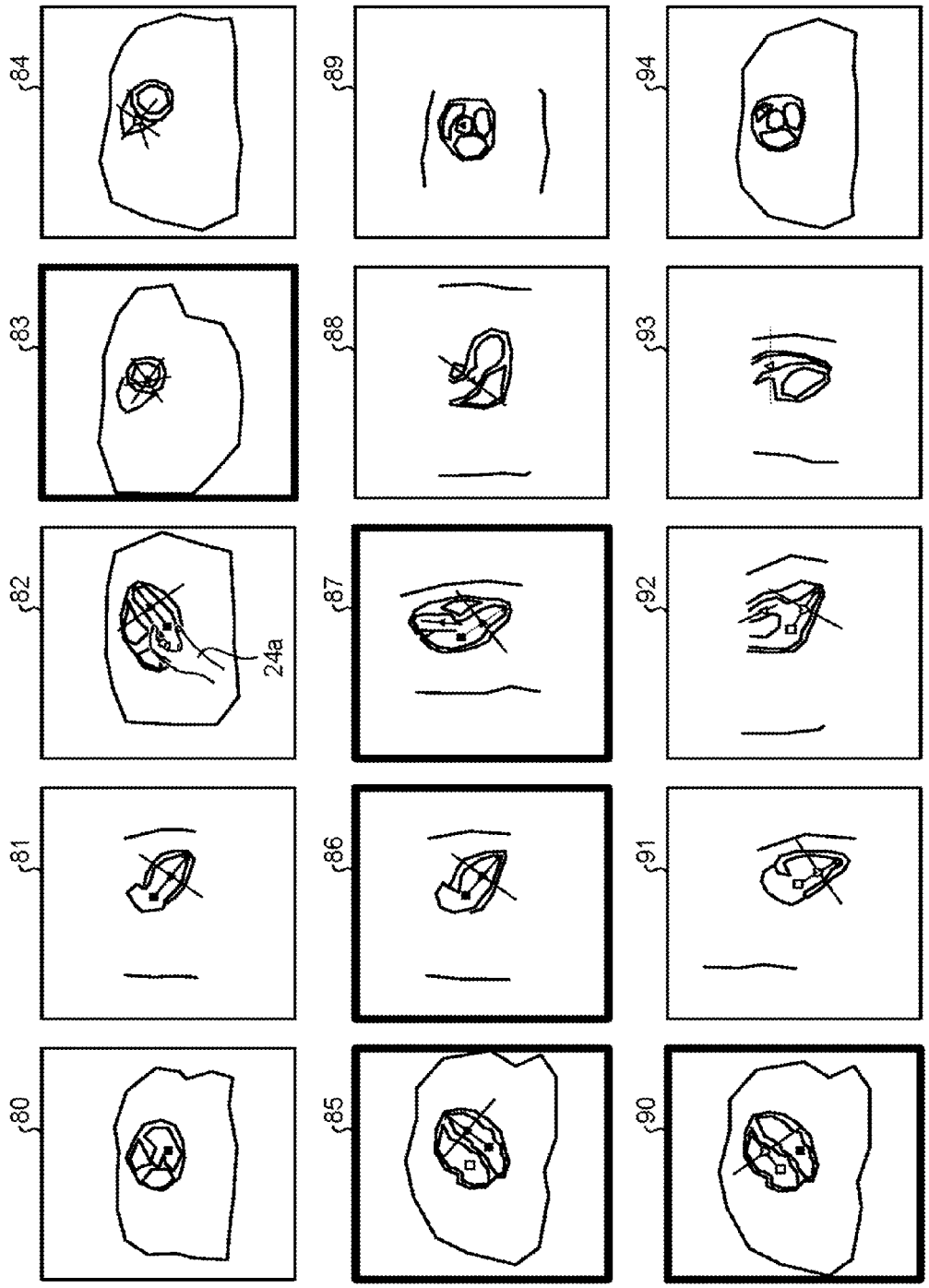
FIG. 10 is a diagram for explaining an example of processing performed by a display control unit when a process returns to Step S6 again in a first modification of the first embodiment.

When the type of the characteristic portion of the reference cross-sectional image 82 the position of which is indicated by the black quadrangle mark the position of which is changed is the mitral valve, requirement for continuing to emphasize the reference cross-sectional image 82 is considered to be low because the position of the mitral valve in the reference cross-sectional image 82 is completely corrected. For this reason, at Step S6, the display control unit 26d cancels emphasis on the reference cross-sectional image 82 as illustrated in FIG. 10. That is, at Step S6, when the position of the black quadrangle mark is changed in the emphasized reference cross-sectional image 82 among the emphasized reference cross-sectional images 82, 83, 85 to 87, and 90 on the display unit 25, the display control unit 26d cancels emphasis on the reference cross-sectional image 82 when the type of the characteristic portion the position of which is indicated by the black quadrangle mark is the same as the type of the characteristic portion the position of which is indicated by the black quadrangle mark the position of which has already been changed in another reference cross-sectional image 81 other than the reference cross-sectional image 82. That is, when the mark corresponding to the mitral valve is selected in the setting operation in the emphasized reference cross-sectional image on the display unit 25, the display control unit 26d cancels emphasis on the emphasized reference cross-sectional image when the position of the mark corresponding to the mitral valve has already been changed in another emphasized reference cross-sectional image other than the emphasized reference cross-sectional image. In this way, emphasis on the reference cross-sectional image 82 is canceled because the position of the mitral valve is completely corrected and the requirement for continuing to be emphasized is considered to be low, and the reference cross-sectional images 83, 85 to 87, and 90 are continued to be emphasized because the position of the mitral valve is not completely corrected and the requirement for continuing to be emphasized is considered to be high. Accordingly, appropriate emphasis can be performed. FIG. 10 is a diagram for explaining an example of processing performed by the display control unit 26d when the process returns to Step S6 again in the first modification of the first embodiment.

Figure 11:
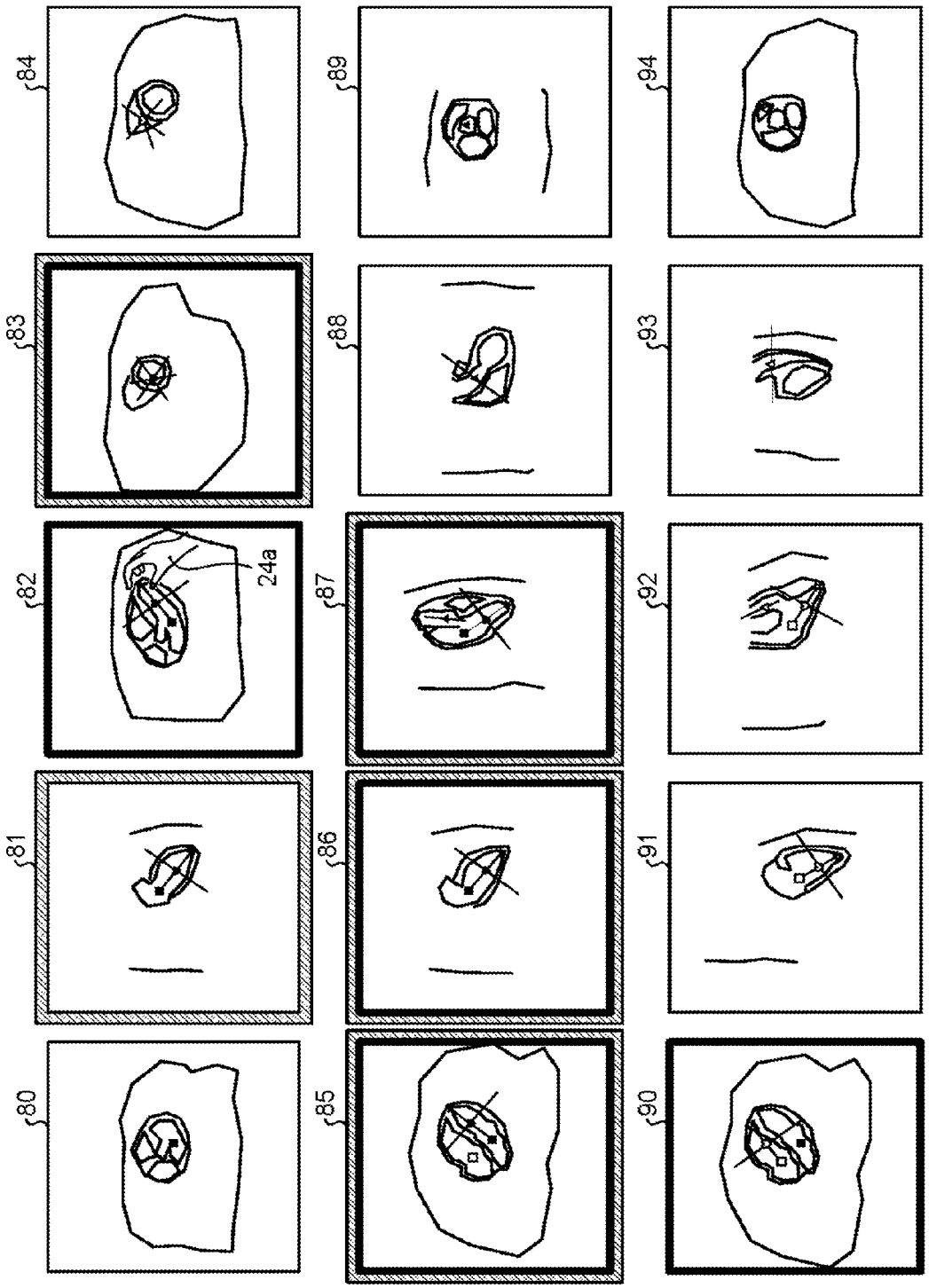
FIG. 11 is a diagram for explaining an example of the processing performed by the display control unit when the process returns to Step S6 again in the first modification of the first embodiment.

On the other hand, when the type of the characteristic portion of the reference cross-sectional image 82 the position of which is indicated by the black star mark the position of which is changed is the left ventricular apex of the heart, the position of the mitral valve in the reference cross-sectional image 82 is not completely corrected, so that the requirement for continuing to emphasize the reference cross-sectional image 82 is considered to be high. For this reason, at Step S6, the display control unit 26d does not cancel emphasis on the reference cross-sectional image 82 as illustrated in FIG. 11. Accordingly, the reference cross-sectional image 82 continues to be emphasized until the position of the mitral valve is corrected. The user thus can take time to grasp the reference cross-sectional image the sectional position of which is changed according to the change of the position of the mark in a certain reference cross-sectional image after the operation of changing the position of the mark is ended. The reference cross-sectional images 82, 83, 85 to 87, and 90 continue to be emphasized because the position of the mitral valve is not completely corrected and the requirement for continuing to be emphasized is considered to be high. Accordingly, appropriate emphasis can be performed. FIG. 11 is a diagram for explaining an example of the processing performed by the display control unit 26d when the process returns to Step S6 again in the first modification of the first embodiment.

When the type of the characteristic portion the position of which is indicated by the black star mark the position of which is changed in the reference cross-sectional image 82 is the left ventricular apex of the heart, at Step S6, the display control unit 26d controls to emphasize the reference cross-sectional images 81, 83, and 85 to 87 the sectional positions of which are defined based on the position of the left ventricular apex of the heart in a display mode different from that of the reference cross-sectional images 82, 83, 85 to 87, and 90 that have been already emphasized. For example, as illustrated in FIG. 11, the display control unit 26d controls to display the reference cross-sectional images 81, 83, and 85 to 87 to which shaded frames are newly provided. That is, when the position of the black star mark is changed in the emphasized reference cross-sectional image 82 among the emphasized reference cross-sectional images 82, 83, 85 to 87, and 90 on the display unit 25, and the type of the characteristic portion the position of which is indicated by the mark the position of which is changed is different from the type of the characteristic portion the position of which is indicated by the black quadrangle mark the position of which has already been changed in another reference cross-sectional image 81 other than the reference cross-sectional image 82, at Step S6, the display control unit 26d controls to emphasize the reference cross-sectional images 81, 83, and 85 to 87 the sectional positions of which are defined using the position of the characteristic portion changed in the reference cross-sectional image 82 as compared with the reference cross-sectional images 82, 84, and 88 to 94 other than the reference cross-sectional images 81, 83, and 85 to 87. When the mark corresponding to the left ventricular apex of the heart is selected in the setting operation in the emphasized reference cross-sectional image on the display unit 25, and the position of the mark corresponding to the left ventricular apex of the heart is not changed in another emphasized reference cross-sectional image other than the emphasized reference cross-sectional image, the display control unit 26d controls to emphasize the other reference cross-sectional images the sectional position of which is defined using the position of the left ventricular apex of the heart. In this way, the display control unit 26d controls to display, in different modes, the reference cross-sectional image emphasized when the mark is selected in the first setting operation and the reference cross-sectional image emphasized when the mark is selected in the second setting operation different from the first setting operation.

Second Modification of First Embodiment

In the first embodiment, described is a case in which, when the mark is designated in a certain reference cross-sectional image and the position of the designated mark is changed, the MRI apparatus 100 causes the reference cross-sectional image to be emphasized. However, the MRI apparatus can also cause a certain reference cross-sectional image to be emphasized when the mark is designated in the reference cross-sectional image. Such an embodiment will be described as a second modification of the first embodiment.

For example, in the second modification, the change unit 26c determines whether the user designates the characteristic portion via the input unit 24. For example, when the pointer 24a is overlapped with the characteristic portion (or the mark), the change unit 26c determines that the characteristic portion (or the characteristic portion the position of which is indicated by the mark) is designated. The change unit 26c then refers to the sectional position definition information table 23a, and specifies the reference cross-sectional image the sectional position of which is defined using the position of the designated characteristic portion.

The display control unit 26d then controls to emphasize the reference cross-sectional image specified by the change unit 26c as compared with the reference cross-sectional images other than the specified reference cross-sectional image.

Figure 12:
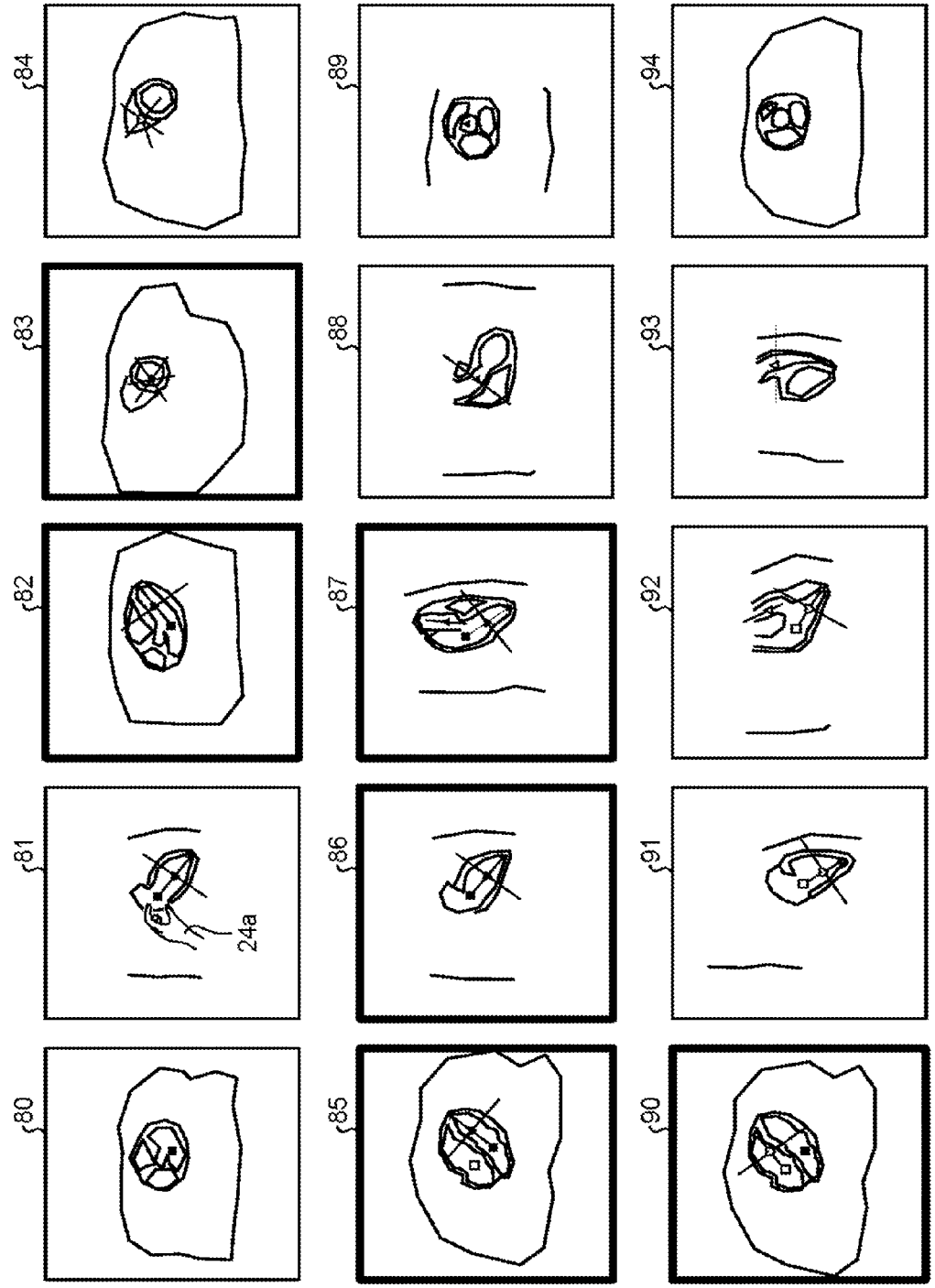
FIG. 12 is a diagram for explaining an example of processing performed by an MRI apparatus according to a second modification of the first embodiment.

For example, in the example of FIG. 2, when the mitral valve in the left ventricular vertical long-axis image 81 is designated, the change unit 26c refers to the sectional position definition information table 23a, and specifies six reference cross-sectional images including the left ventricular horizontal long-axis image 82, the left ventricular short-axis image 83, the left ventricular 4-chamber long-axis image 85, the left ventricular 2-chamber long-axis image 86, the left ventricular 3-chamber long-axis image 87, and the right ventricular 4-chamber long-axis image 90 the sectional positions of which are defined using the position of the designated mitral valve. As illustrated in FIG. 12, the display control unit 26d then controls to emphasize the specified six reference cross-sectional images as compared with the reference cross-sectional images 81, 84, 88, and 91 to 94 other than the specified six reference cross-sectional images. FIG. 12 is a diagram for explaining an example of processing performed by the MRI apparatus according to the second modification of the first embodiment. In this way, before the position of the characteristic portion is changed, the display control unit 26d controls to emphasize the reference cross-sectional image the sectional position of which is defined using the position of the designated characteristic portion as compared with the other reference cross-sectional images. With the MRI apparatus according to the second modification, the user thus can grasp, before the position of a certain characteristic portion is changed, the reference cross-sectional image the sectional position of which is to be changed if the position of the characteristic portion is changed. Accordingly, with the MRI apparatus according to the second modification, the user can more easily perform positioning of the reference cross-sectional image. In the second modification, described is the example in which emphasis is performed when the characteristic portion is designated (example in which emphasis is canceled when the position of the mark indicating the characteristic portion is started to be changed). However, the embodiment is not limited thereto. The position of the mark is started to be changed after the characteristic portion is designated, and the various embodiments described above may be combined for emphasis thereafter.

Second Embodiment

In the first embodiment, described is a case of emphasizing the reference cross-sectional images as targets of emphasis in the same degree. However, the MRI apparatus may also cause the reference cross-sectional images to be emphasized as targets of emphasis in a plurality of degrees. Such an embodiment will be described as a second embodiment.

In the second embodiment, for example, when the position of the characteristic portion is changed in a certain reference cross-sectional image, the display control unit 26d first calculates a degree of change of the sectional position due to the change of the position of the characteristic portion for another reference cross-sectional image the sectional position of which is defined using the characteristic portion the position of which is changed.

For example, the following describes a case in which the user changes the position of the mitral valve in the left ventricular vertical long-axis image 81 in the example of FIG. 2. In this case, the display control unit 26d calculates the degree of change of the sectional position due to the change of the position of the mitral valve for each of the six reference cross-sectional images including the left ventricular horizontal long-axis image 82, the left ventricular short-axis image 83, the left ventricular 4-chamber long-axis image 85, the left ventricular 2-chamber long-axis image 86, the left ventricular 3-chamber long-axis image 87, and the right ventricular 4-chamber long-axis image 90 the sectional positions of which are defined using the position of the mitral valve.

The following describes an example of a method of calculating the degree of change of the sectional position due to the change of the position of the mitral valve for each of the six reference cross-sectional images. For example, the display control unit 26d calculates an angle between a motion vector of the mitral valve due to the change of the position and a normal vector of each of the six reference cross-sectional images. The normal vector of each of the six reference cross-sectional images is calculated as the cross product of the two unit vectors u and v orthogonal to each other. In this case, as the calculated angle comes close to 90 degrees, the degree of change of the sectional position due to the change of the position of the mitral valve is reduced. When the calculated angle is equal to or larger than (90−α) degrees and equal to or smaller than (90+α) degrees, the sectional position is considered to be not much changed, so that the display control unit 26d controls to emphasize the reference cross-sectional image in a predetermined small degree. On the other hand, when the calculated angle is smaller than (90−α) degrees or larger than (90+α) degrees, the sectional position is considered to be much changed, so that the display control unit 26d controls to emphasize the reference cross-sectional image in a predetermined large degree.

Figure 13:
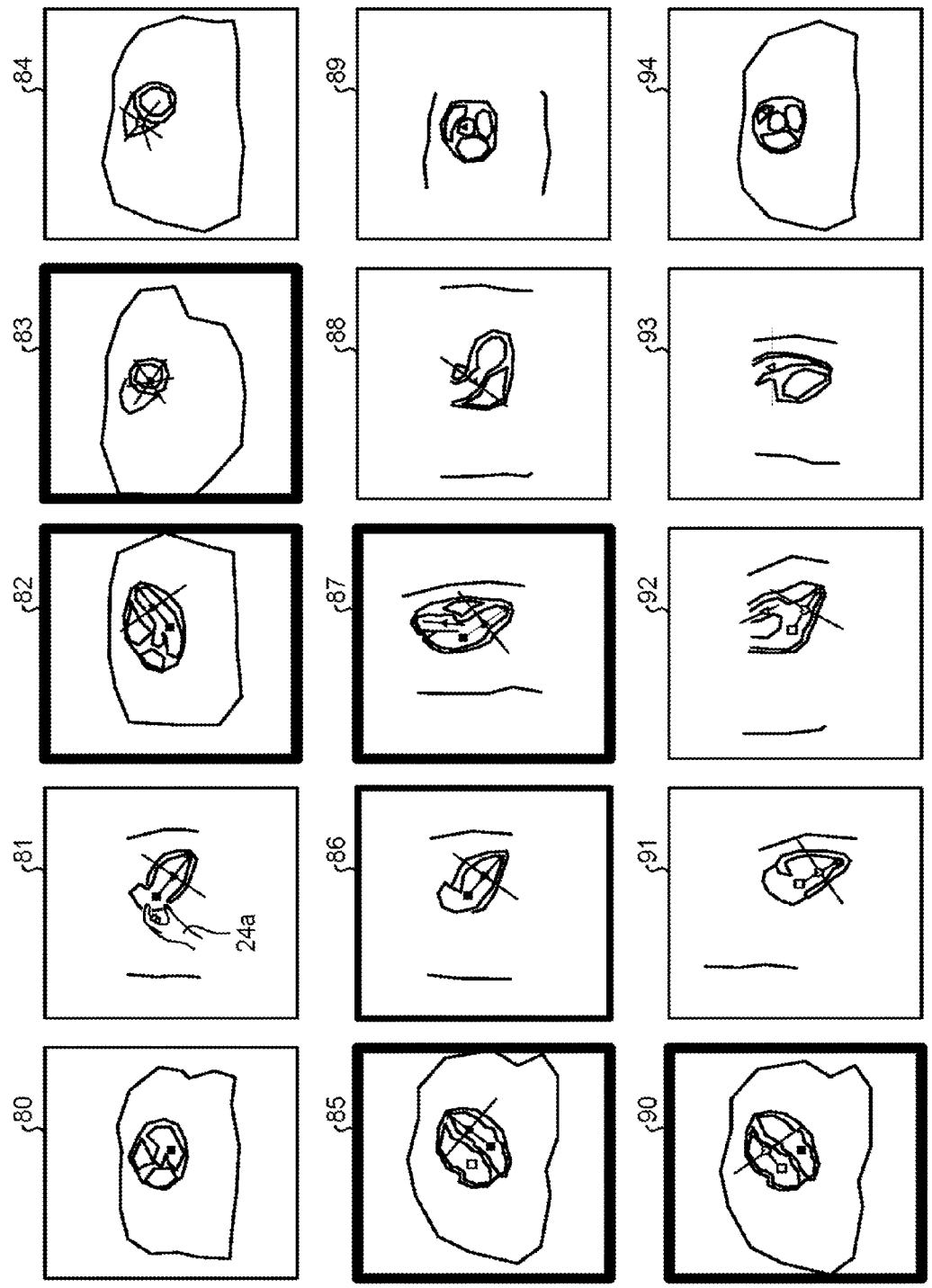
FIG. 13 is a diagram for explaining an example of processing performed by an MRI apparatus according to a second embodiment.

FIG. 13 is a diagram for explaining an example of processing performed by the MRI apparatus according to the second embodiment. For example, the display control unit 26d controls to emphasize the reference cross-sectional images 82, 83, 85, 87, and 90 the calculated angle of which is smaller than (90−α) degrees or larger than (90+α) degrees so that the thickness of the frame thereof is a first predetermined value as illustrated in the example of FIG. 13. The user can set an arbitrary value to a. As illustrated in the example of FIG. 13, the display control unit 26d controls to emphasize the reference cross-sectional image 86 the calculated angle of which is equal to or larger than (90−α) degrees and equal to or smaller than (90+α) degrees so that the thickness of the frame thereof is a second predetermined value that is smaller than the first predetermined value. A method of changing the degree of emphasis is not limited thereto. For example, the degree of emphasis may be continuously changed using a difference between the calculated angle and 90 degrees as a parameter. Alternatively, a color to be emphasized may be changed depending on the degree. In this way, in the MRI apparatus according to the second embodiment, the display control unit 26d controls to emphasize the other reference cross-sectional images the sectional positions of which are defined using the characteristic portion the position of which is changed in a degree corresponding to the degree of change of the sectional position. That is, in the MRI apparatus according to the second embodiment, when the position of the mark is changed in the setting operation, the display control unit 26d calculates the degree of change of the sectional position in the reference cross-sectional image the sectional position of which is defined using the characteristic portion corresponding to the mark, and controls to emphasize the reference cross-sectional image in a degree corresponding to the calculated degree of change. With the MRI apparatus according to the second embodiment, the user thus can easily grasp the reference cross-sectional image the sectional position of which is changed according to the change of the position of the characteristic portion in a certain reference cross-sectional image, and can also easily grasp the degree of change in display of the reference cross section the sectional position of which is changed. Accordingly, with the MRI apparatus according to the second embodiment, the user can more easily perform positioning of the reference cross-sectional image.

Third Embodiment

The MRI apparatus can fix the sectional position of a certain reference cross-sectional image. That is, the MRI apparatus can prevent the sectional position of a certain reference cross-sectional image from being changed irrespective of the change of the characteristic portion of another reference cross-sectional image. Due to this, the reference cross sectional position that is already within a permissible range is fixed and excluded, so that the number of cross sections to be confirmed in a subsequent correction operation can be reduced, which reduces a burden on the operator. Such an embodiment will be described as a third embodiment.

In the MRI apparatus according to the third embodiment, when a plurality of reference cross-sectional images are displayed on the display unit 25 by the generation unit 26b and the like, the user inputs, via the input unit 24, an instruction to fix the sectional position of at least one of the displayed reference cross-sectional images. The display control unit 26d then controls to emphasize the reference cross-sectional image the sectional position of which is fixed indicated by the input instruction as compared with the other reference cross-sectional images.

Figure 14:
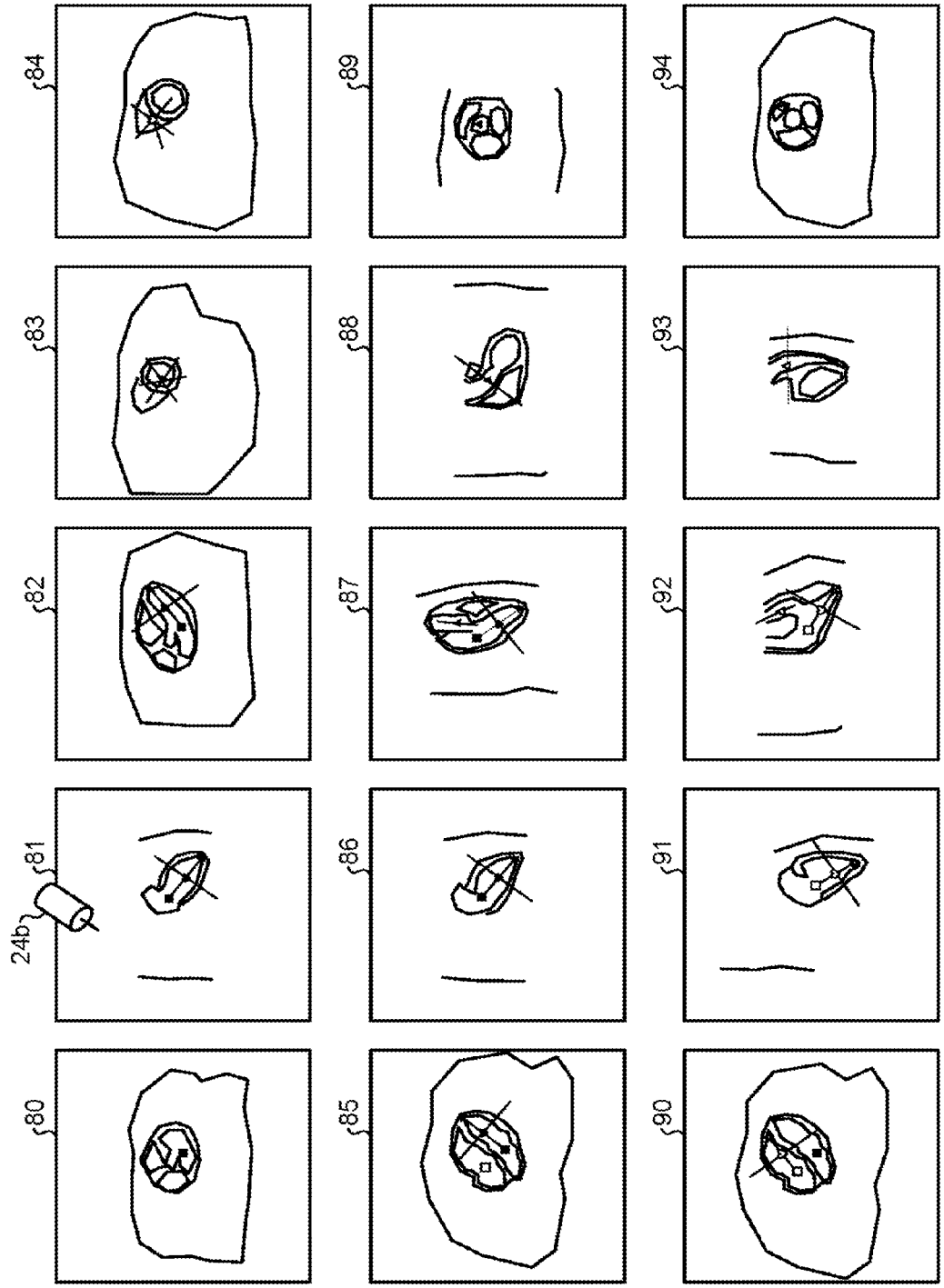
FIG. 14 is a diagram for explaining an example of processing performed by an MRI apparatus according to a third embodiment.

FIG. 14 is a diagram for explaining an example of processing performed by the MRI apparatus according to the third embodiment. For example, when the instruction to fix the sectional position of the reference cross-sectional image 81 is input, the display control unit 26d superimposes an image 24b representing a pin on the reference cross-sectional image 81 to emphasize the reference cross-sectional image 81 as compared with the reference cross-sectional images 82 to 94. The method of emphasis is not limited to the method of superimposing the image representing a pin on the reference cross-sectional image. The method of emphasis is optional. For example, it is effective to collect only images representing a pin as a layout using another window because the reference cross section the position of which is fixed and the other reference cross sections can be easily confirmed and movement of a visual point is reduced, which reduces the burden on the operator.

Even when the position of the characteristic portion such as the mitral valve and the left ventricular apex of the heart that defines the sectional position of the reference cross-sectional image 81 is changed in the reference cross-sectional images 82 to 94 other than the reference cross-sectional image 81, the display control unit 26d does not change the sectional position of the reference cross-sectional image 81. That is, when the instruction to fix the sectional position of at least one of the listed reference cross-sectional images is input in the setting operation, the display control unit 26d controls to emphasize the at least one of the reference cross-sectional images. Even when the position of the mark corresponding to the characteristic portion that defines the sectional position of the at least one of the reference cross-sectional images is changed in the setting operation, the display control unit 26d does not change the sectional position of the at least one of the reference cross-sectional images. In this way, with the MRI apparatus according to the third embodiment, the user can fix the sectional position of a certain reference cross-sectional image. Accordingly, with the MRI apparatus according to the third embodiment, the user can more easily perform positioning of the reference cross-sectional image.

Other Embodiments

The embodiment is not limited to the first to the third embodiments described above.

Target Portion

In the first to the third embodiments described above, the "heart" is exemplified as the target portion. However, the embodiment is not limited thereto. For example, the embodiment can be similarly applied to a case of testing other target portions such as a "brain", joints including a "shoulder" and a "knee", internal organs other than the heart, and various circulatory organs.

Figure 15:
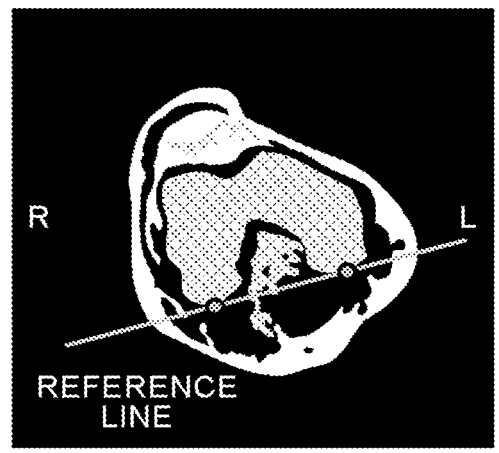
FIG. 15 is a diagram for explaining an example of a method of setting various reference cross sections when a "knee" is set to be a target portion according to the embodiment.
Figure 16:
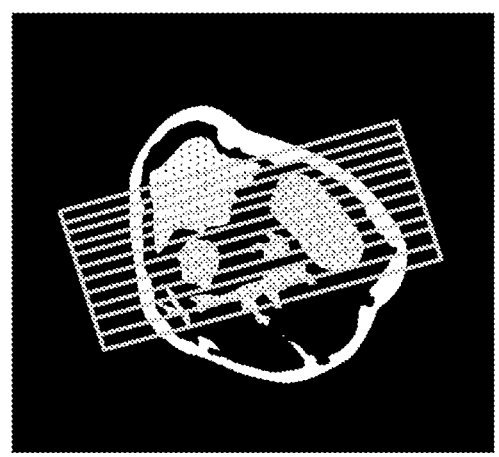
FIG. 16 is a diagram for explaining an example of the method of setting various reference cross sections when the "knee" is set to be the target portion according to the embodiment.
Figure 17:
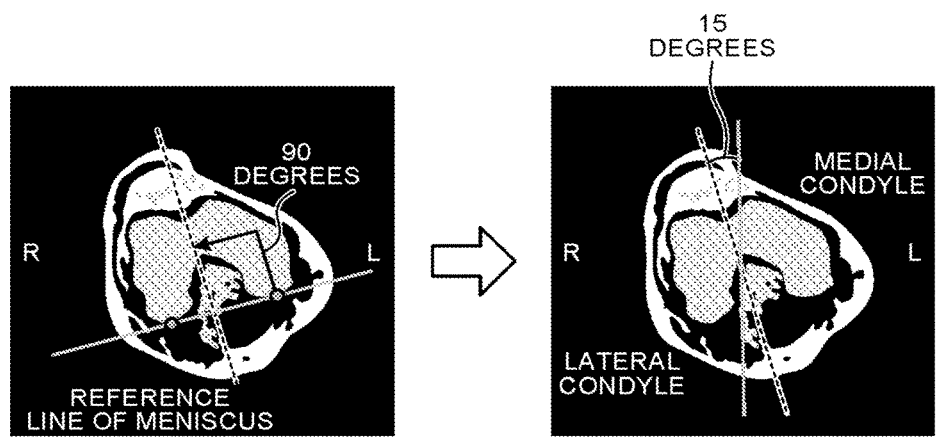
FIG. 17 is a diagram for explaining an example of the method of setting various reference cross sections when the "knee" is set to be the target portion according to the embodiment.

For example, when the "knee" is set to be the target portion, a coronal cross section of the knee is set based on positions of two characteristic points that are back side edges of a medial condyle and a lateral condyle of femur. FIGS. 15 to 17 are diagrams for explaining an example of a method of setting various reference cross sections when the "knee" is set to be the target portion in the embodiment. For example, as illustrated in FIG. 15, a reference line connecting the two characteristic points is set. Subsequently, as illustrated in FIG. 16, a coronal cross section is set to be parallel with the reference line and parallel with the head-foot direction.

A cross section along an anterior cruciate ligament is set based on the reference line. For example, as illustrated in FIG. 17, the reference line is rotated by 90 degrees about a head-foot axis, a reference axis is rotated by an angle of about 15 degrees, and a section including the reference axis that is parallel with the head-foot direction is set to be the section along the anterior cruciate ligament.

Crossing Line

In the first to the third embodiments described above, described is a case of emphasizing the reference cross-sectional image when the characteristic portion is designated or the position of the characteristic portion is changed. However, the embodiment is not limited thereto. For example, the MRI apparatus can cause the reference cross-sectional image to be emphasized when the crossing line is designated or the position of the crossing line is changed.

Similarly to a case of designating the characteristic portion by designating the mark indicating the position of the characteristic portion and a case of changing the position of the characteristic portion by changing the position of the mark indicating the position of the characteristic portion, the user can designate the crossing line by designating the mark of the crossing line, or can change the position of the crossing line by changing the position of the mark of the crossing line.

Figure 18:
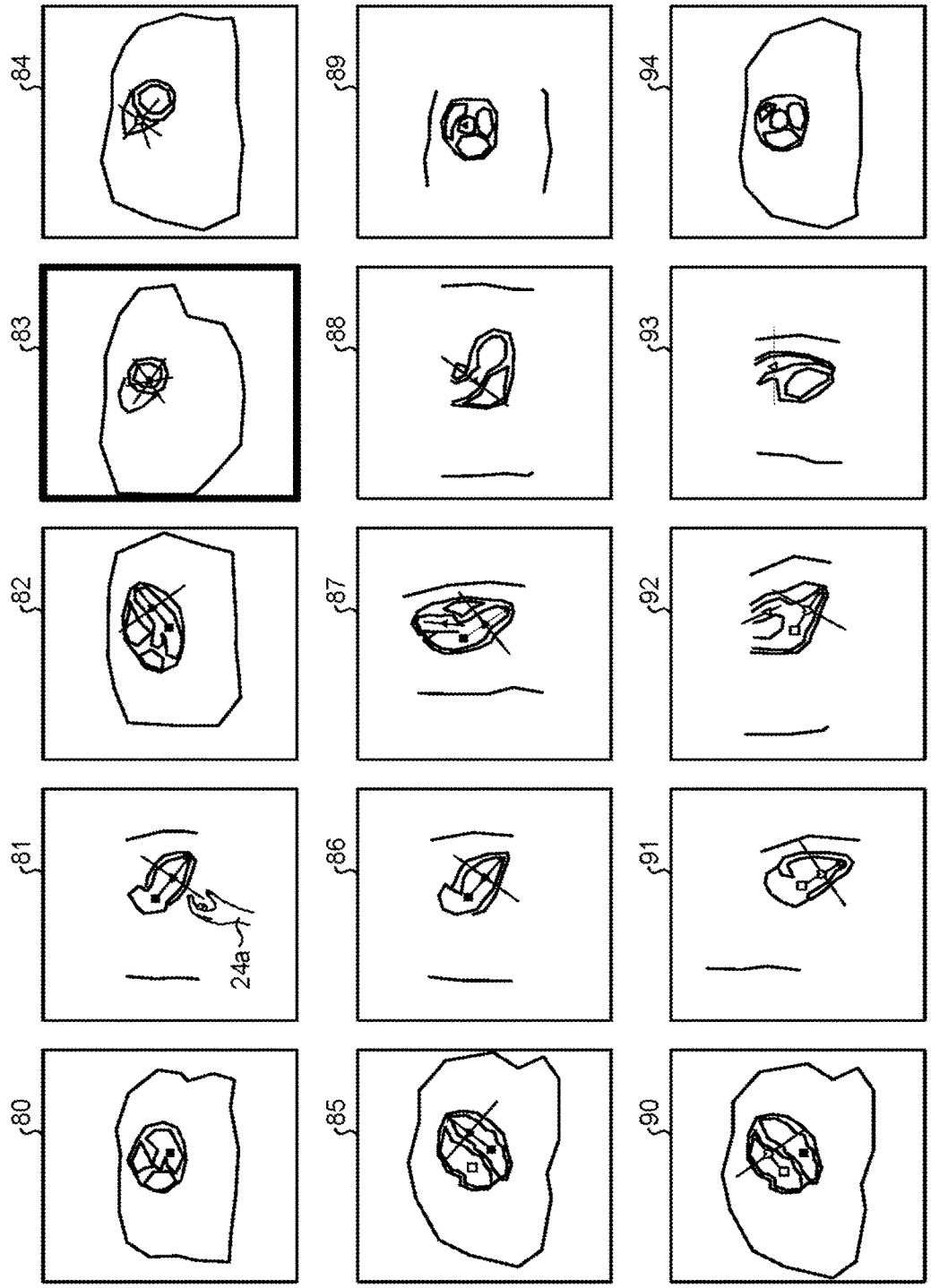
FIG. 18 is a diagram for explaining an example of a case in which the reference cross-sectional image is emphasized when a crossing line according to the embodiment is designated.

For example, when the crossing line at which the sectional position of a certain reference cross-sectional image crosses the sectional position of another reference cross-sectional image is designated in the former reference cross-sectional image, the display control unit 26d controls to emphasize the other reference cross-sectional image as compared with the reference cross-sectional images other than the other reference cross-sectional image. FIG. 18 is a diagram for explaining an example of a case in which the reference cross-sectional image is emphasized when the crossing line according to the embodiment is designated.

As illustrated in the example of FIG. 18, in the left ventricular vertical long-axis image 81, displayed are two types of lines including a long axis connecting the mitral valve with the left ventricular apex of the heart and the crossing line with respect to the left ventricular short-axis image. When a crossing line position of the long axis is corrected, the positions of the mitral valve and the left ventricular apex of the heart are corrected at the same time, and a related sectional position is changed. When the crossing line with respect to the left ventricular short-axis image is corrected, the sectional position of the left ventricular short-axis image 83 is changed.

In the example of FIG. 18, when the crossing line with respect to the left ventricular short-axis image 83 on the left ventricular vertical long-axis image 81 is designated, the left ventricular short-axis image 83 is emphasized as compared with the other reference cross-sectional images 81, 82, and 84 and 94. Accordingly, the user can easily grasp, before the position of the crossing line is actually changed, the reference cross-sectional image the sectional position of which is changed according to the change of the position of the crossing line in a certain reference cross-sectional image. The user thus can easily perform positioning of the reference cross-sectional image.

Similarly, when the position of the crossing line at which the sectional position of a certain reference cross-sectional image crosses the sectional position of another reference cross-sectional image is changed in the former reference cross-sectional image, the display control unit 26d can control to emphasize the other reference cross-sectional image as compared with the reference cross-sectional images other than the other reference cross-sectional image. That is, when the crossing line at which the sectional position of one of the listed reference cross-sectional images crosses the sectional position of the other reference cross-sectional image is selected in the setting operation, the display control unit 26d controls to emphasize the other reference cross-sectional image described above.

Types of Reference Cross-Sectional Images

In the first to the third embodiments described above, 14 types of reference cross-sectional images are assumed to be used in the test. However, the embodiment is not limited thereto. Other various types of reference cross-sectional images may be used.

With the magnetic resonance imaging apparatus according to at least one of the embodiments described above, the user can easily perform positioning of the reference cross-sectional image.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus comprising: processing circuitry configured to
generate a plurality of cross-sectional images for setting a sectional position to be collected in main imaging based on a characteristic portion of a target detected in three-dimensional data,
list the cross-sectional images on a display and superimpose a mark corresponding to the characteristic portion on at least one of the cross-sectional images,
receive a setting operation to determine the sectional position,
cause, when the mark is selected in the setting operation, a cross-sectional image among the listed cross-sectional images to be emphasized, a sectional position of the cross-sectional image being defined using the characteristic portion corresponding to the mark, and
perform main imaging based on the sectional position after the setting operation, wherein
when the position of the mark is changed in the setting operation, the processing circuitry calculates an angle using the characteristic portion corresponding to the mark, the angle being an angle between a vector corresponding to a change of the position and a normal vector of the cross-sectional image, and the processing circuitry causes the cross-sectional image to be emphasized in a degree corresponding to the calculated angle.

2. The apparatus according to claim 1, wherein, while the position of the mark is being changed in the setting operation, the processing circuitry causes the cross-sectional image to be emphasized the sectional position of which is defined using the characteristic portion corresponding to the mark among the listed cross-sectional images.

3. The apparatus according to claim 1, wherein the processing circuitry continues to cause the cross-sectional image to be emphasized the sectional position of which is defined using the characteristic portion corresponding to the mark among the listed cross-sectional images even after the setting operation is finished in addition to a period in which the position of the mark is being changed in the setting operation.

4. The apparatus according to claim 3, wherein, when the mark corresponding to a first the characteristic portion is selected in the setting operation in the emphasized cross-sectional image on the display and the position of the mark corresponding to the first characteristic portion has already been changed in another emphasized cross-sectional image other than the former emphasized cross-sectional image, the processing circuitry cancels emphasis on the emphasized cross-sectional image.

5. The apparatus according to claim 3, wherein, when the mark corresponding to the characteristic portion is selected in the setting operation in the emphasized cross-sectional image on the display and the position of the mark corresponding to the characteristic portion is not changed in another emphasized cross-sectional image other than the former emphasized cross-sectional image, the processing circuitry causes another cross-sectional image to be emphasized the sectional position of which is defined using the position of the characteristic portion.

6. The apparatus according to claim 1, wherein, when the characteristic portion related to the target is selected in the setting operation, the processing circuitry causes the cross-sectional image to be emphasized the sectional position of which is defined using the characteristic portion among the listed cross-sectional images.

7. The apparatus according to claim 1, wherein
the processing circuitry
superimposes information indicating a position of the characteristic portion on at least one of the listed cross-sectional images, and
causes another cross-sectional image to be emphasized the sectional position of which is defined with the information when the information is changed in the setting operation.

8. The apparatus according to claim 1, wherein, when an instruction to fix the sectional position of at least one of the listed cross-sectional images is input in the setting operation, the processing circuitry causes the at least one of the cross-sectional images to be emphasized, and does not change the sectional position of the at least one cross-sectional image even when the position of the mark corresponding to the characteristic portion that defines the sectional position of the at least one cross-sectional image is changed in the setting operation in a cross-sectional image other than the at least one cross-sectional image.

9. The apparatus according to claim 1, wherein the processing circuitry causes the cross-sectional image emphasized when the mark is selected in a first setting operation and the cross-sectional image emphasized when the mark is selected in a second setting operation different from the first setting operation to be displayed in different modes.

10. An medical image processing method comprising:
generating a plurality of cross-sectional images for setting a sectional position to be collected in main imaging based on a characteristic portion of a target detected in three-dimensional data;
listing the cross-sectional images on a display and superimposing a mark corresponding to the characteristic portion on at least one of the cross-sectional images;
receiving a setting operation to determine the sectional position;
causing, when the mark is selected in the setting operation, a cross-sectional image to be emphasized a sectional position of which is defined using the characteristic portion corresponding to the mark among the listed cross-sectional images; and
performing main imaging based on the sectional position after the setting operation, wherein the method comprises:
when the position of the mark is changed in the setting operation, calculating an angle using the characteristic portion corresponding to the mark, the angle being an angle between a vector corresponding to a change of the position and a normal vector of the cross-sectional image, and
causing the cross-sectional image to be emphasized in a degree corresponding to the calculated angle.

* * * * *